(12) United States Patent
Borchert et al.

(10) Patent No.: US 8,945,826 B2
(45) Date of Patent: Feb. 3, 2015

(54) HEAT-STABLE CARBONIC ANHYDRASES AND THEIR USE

(75) Inventors: Martin Borchert, Alleroed (DK); Paria Saunders, Knightdale, NC (US)

(73) Assignees: Novozymes A/S, Bagsvaerd (DK); Novozymes North America Inc, Franklinton, NC (US)

( * ) Notice: Subject to any disclaimer, the term of this patent is extended or adjusted under 35 U.S.C. 154(b) by 335 days.

(21) Appl. No.: 13/379,294

(22) PCT Filed: Jun. 25, 2010

(86) PCT No.: PCT/US2010/040022
§ 371 (c)(1),
(2), (4) Date: Dec. 19, 2011

(87) PCT Pub. No.: WO2010/151787
PCT Pub. Date: Dec. 29, 2010

(65) Prior Publication Data
US 2012/0107899 A1 May 3, 2012

Related U.S. Application Data

(60) Provisional application No. 61/220,636, filed on Jun. 26, 2009.

(51) Int. Cl.
| | | |
|---|---|---|
| C12Q 1/00 | (2006.01) | |
| B01D 53/84 | (2006.01) | |
| B01D 53/62 | (2006.01) | |
| C12N 9/88 | (2006.01) | |
| C12P 7/40 | (2006.01) | |

(52) U.S. Cl.
CPC ............. *B01D 53/84* (2013.01); *B01D 53/62* (2013.01); *C12N 9/88* (2013.01); *C12P 7/40* (2013.01); *B01D 2251/95* (2013.01); *B01D 2257/504* (2013.01); *Y02C 10/02* (2013.01); *Y02C 10/04* (2013.01); *Y02E 50/12* (2013.01)
USPC ............................................................ 435/4

(58) Field of Classification Search
USPC ............................................................ 435/4
See application file for complete search history.

(56) References Cited

U.S. PATENT DOCUMENTS

| | | |
|---|---|---|
| 6,143,556 A | 11/2000 | Trachtenberg |
| 6,524,842 B1 | 2/2003 | Vainberg |
| 7,132,090 B2 | 11/2006 | Dziedzic |
| 2004/0029257 A1 | 2/2004 | Dutil |

(Continued)

FOREIGN PATENT DOCUMENTS

| | | |
|---|---|---|
| WO | 2004007058 A1 | 1/2004 |
| WO | 2004028667 A1 | 4/2004 |

(Continued)

OTHER PUBLICATIONS

Badger et al. Annu. Rev. Plant Physiol. Plant Mol. Biol. 1994, 45:369-392.*

(Continued)

*Primary Examiner* — Bin Shen
(74) *Attorney, Agent, or Firm* — Elias Lambiris

(57) ABSTRACT

The present invention relates to use of *Caminibacter* carbonic anhydrase in CO$_2$ extraction, e.g., from flue gas, natural gas, biogas or ambient air. The *Caminibacter* carbonic anhydrases are especially well suited for these purpose due to their extreme thermostability.

20 Claims, 2 Drawing Sheets

(56) References Cited

U.S. PATENT DOCUMENTS

| | | |
|---|---|---|
| 2005/0014936 A1 | 1/2005 | Fraser |
| 2008/0003662 A1 | 1/2008 | Trachtenberg |

FOREIGN PATENT DOCUMENTS

| | | | |
|---|---|---|---|
| WO | 2004104160 | A1 | 12/2004 |
| WO | 2005114417 | A2 | 12/2005 |
| WO | 2006089423 | A1 | 8/2006 |
| WO | 2008095057 | A2 | 8/2008 |
| WO | 2010014773 | A1 | 2/2010 |

OTHER PUBLICATIONS

Kohl and Nielsen, Gas Purification, 5th ed., Gulf Professional Publishing, Houston, TX, 1997.

Vetriani et al, 2007, Database UniProt, Access No. A6DCH2.

Voordeckers et al, 2005, Int J Syst Evolut Microbiol 55(2), 773-779.

* cited by examiner

HEAT-STABLE CARBONIC ANHYDRASES AND THEIR USE

CROSS-REFERENCE TO RELATED APPLICATIONS

This application is a 35 U.S.C. 371 national application of PCT/US2010/040022 filed Jun. 25, 2010, which claims priority or the benefit under 35 U.S.C. 119 of U.S. provisional application No. 61/220,636 filed Jun. 26, 2009, the contents of which are fully incorporated herein by reference.

FIELD OF THE INVENTION

The present invention relates to use of carbonic anhydrases obtainable from *Caminibacter* in $CO_2$ extraction, e.g., from flue gasses, biogas, natural gas or ambient air. The invention also relates to bioreactors for extracting carbon dioxide and compositions useful for such extraction processes. The present invention furthermore relates to carbonic anhydrases.

BACKGROUND OF THE INVENTION

Carbon dioxide ($CO_2$) emissions are a major contributor to the phenomenon of global warming. $CO_2$ is a by-product of combustion and it creates operational, economic, and environmental problems. $CO_2$ emissions may be controlled by capturing $CO_2$ gas before emitted into the atmosphere. There are several chemical approaches to control the $CO_2$ emissions (A. Kohl and R. Nielsen, Gas Purification, $5^{th}$ ed., Gulf Professional Publishing, Houston, Tex., 1997). However, many of these approaches have drawbacks such as high energy consumption, slow processes, and use of ecologically questionable or toxic compounds.

An enzyme based approach using the capability of carbonic anhydrase to catalyze the conversion of $CO_2$ to bicarbonate at a very high rate (turnover is up to $10^5$ molecules of $CO_2$ per second), overcomes the reaction rates and environmental issues in relation to $CO_2$ capture. Technical solutions for extracting $CO_2$ from gases, such as combustion gases or respiration gases, using carbonic anhydrases have been described in WO 2006/089423, U.S. Pat. No. 6,524,842, WO 2004/007058, WO 2004/028667, US 2004/0029257, U.S. Pat. No. 7,132,090, WO 2005/114417, U.S. Pat. No. 6,143,556, WO 2004/104160, US 2005/0214936; WO 2008/095057. Generally, these techniques operate by bringing a soluble or immobilized carbonic anhydrase into contact with $CO_2$ which either may be in a gas phase or a liquid phase. In the presence of water, carbonic anhydrase catalyzes the conversion of $CO_2$ into bicarbonate ions which may be further protonated or deprotonated to carbonic acid and/or carbonate ions depending on the pH of the medium. The ions may either be utilized to facilitate growth of algae or microorganisms that utilize bicarbonate/carbonate as a carbon source, to induce a pH change in a surrounding medium or supply buffering capacity, to provide bicarbonate/carbonate as an active agent for subsequent chemical processes, or precipitated as a carbonate salt, or converted back into pure $CO_2$, which can then be used (for example in enhanced oil recovery, for production of urea, for food and beverage processing, or to supply $CO_2$ to greenhouses or cultivation ponds), released (for example from a contained life support environment such as a submarine, spacecraft, or artificial lung), compressed (for example for transportation through pipelines), or stored (such as in geological or deep oceanic formations or saline aquifers).

Mammalian, plant and prokaryotic carbonic anhydrases (alpha- and beta-class CAs) generally function at physiological temperatures (37° C.) or lower temperatures. The temperature of combustion gasses or the liquids into which they are dissolved may, however, easily exceed the temperature optimum for the carbonic anhydrase used to capture the $CO_2$. One of the drawbacks of using enzyme based solutions is that extensive cooling may be needed in $CO_2$ extraction processes prior to contacting the $CO_2$-containing gas/liquid with the carbonic anhydrase, and cooling is an energy consuming process. Consequently, there is a need for more heat-stable carbonic anhydrases when the enzyme is to be used under industrially relevant conditions.

SUMMARY OF THE INVENTION

One aspect of the present invention is the use of carbonic anhydrases derived from or producible by bacteria of the genus *Caminibacter*, for extraction of carbon dioxide from a carbon dioxide-containing medium. The carbonic anhydrases used in the present invention maintain a least 30%, preferably at least 40% residual activity after 15 minutes, preferably 2 hours in 0.1 M Britton-Robinson buffer pH 8.0 at temperatures at or above 55° C., preferably at or above 60° C., preferably at or above 65° C., more preferably at or above 70° C., 75° C., 80° C., or 85° C., even more preferably at or above 90° C. and most preferably above 100° C. The heat-stable carbonic anhydrases are in particular used in a bioreactor capable of extracting $CO_2$ emitted from combustion, or from raw natural gas or a syngas or a biogas or ambient air when conditions in the extraction process require the enzyme to be exposed to high temperatures. The enzymes may, however, also be employed in processes which do not occur at elevated temperatures, since they also maintain activity at lower temperatures, e.g., 0° C., room temperature (20 to 25° C.) and 37° C. The heat stability is also useful when exposing carbonic anhydrase to high temperature environments (i.e., where the temperature exceeds 45° C., 50° C. or even 55° C.) during manufacture, use, or idle periods, for example storage in a hot warehouse. Heat stability during use may include situations where carbonic anhydrase carries out catalysis at one temperature (e.g., 45° C., 50° C., 55° C., 60° C. or 65° C.) and then, due to different stage(s) in the process, is exposed to higher temperatures (e.g., 70° C., 75° C., 80° C., 85° C., 90° C. or 100° C.)) where it either also carries out catalysis or remains idle until exposed to a next stage of the process, such as at a lower temperature, where carbonic anhydrase again carries out catalysis. In these situations, carbonic anhydrase may have to withstand repeated exposure to lower and higher temperatures during the process of use, hence a heat stable carbonic anhydrase is needed.

In a further aspect, the invention provides a composition comprising a matrix suitable for immobilization and a carbonic anhydrase derived from or producible by bacteria of the genus *Caminibacter*.

In a further aspect, the present invention provides a bioreactor suitable for extracting carbon dioxide.

DETAILED DESCRIPTION OF THE INVENTION

Figure 1:
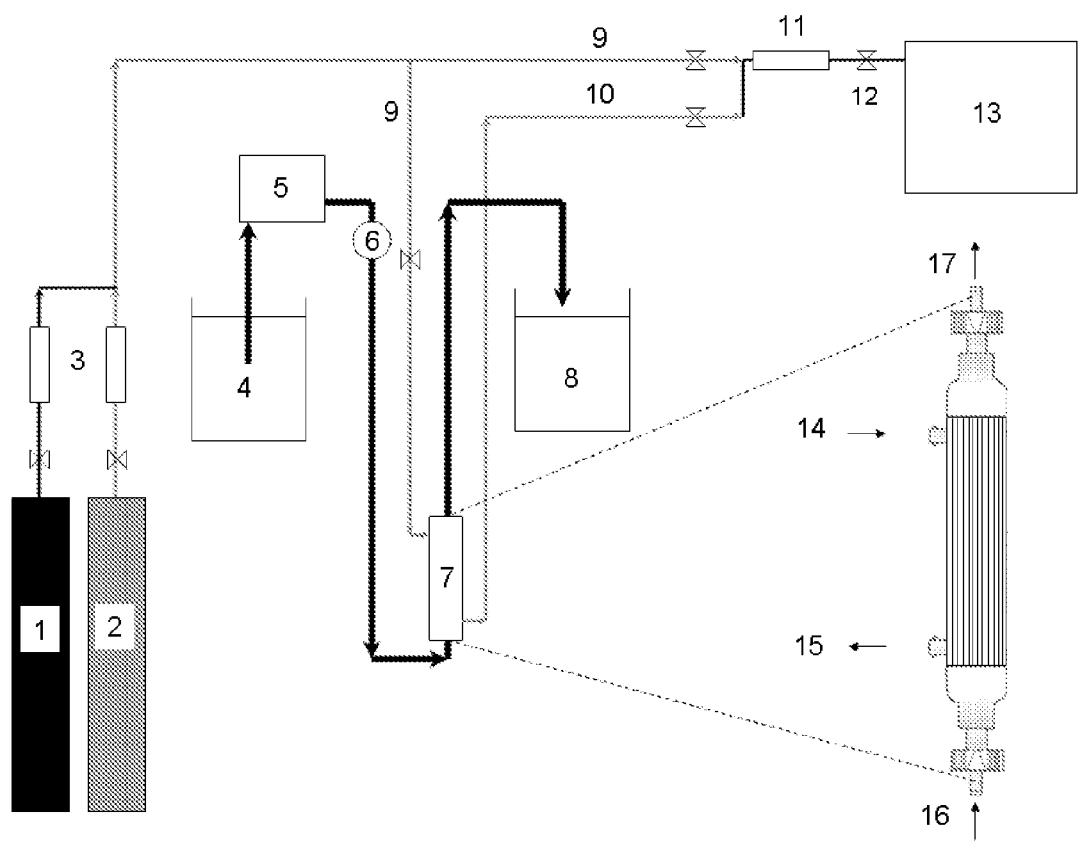
FIG. 1 is a schematic presentation of a hollow fiber membrane bioreactor. The numbers represent the following features: 1. Carbon Dioxide ($CO_2$) tank; 2. Nitrogen ($N_2$) tank; 3. Mass flow controllers (MFC); 4. Carrier liquid reservoir; 5. Liquid pump; 6. Pressure gauge; 7. Hollow fiber membrane module; 8. Waste; 9. Feed gas; 10. Scrubbed gas; 11. Mass flow meter (MFM); 12. Gas sampling valve; 13. Gas chromatograph; 14. Feed gas in; 15. Scrubbed gas out; 16. Liquid in; 17. Liquid out.

One aspect of the present invention concerns the use of a carbonic anhydrase obtainable from or producible by bacteria strains of the genus *Caminibacter* for the extraction of $CO_2$ from $CO_2$-containing media, such as a gas, a liquid or multiphase mixture. The present invention is in particular useful where the temperature of the $CO_2$-containing medium is above the temperature optimum for commercially available carbonic anhydrases, such as CA-I or CA-II isolated from human or bovine erythrocytes.

DEFINITIONS

The term "carbonic anhydrase activity" or "CA activity" is defined herein as an EC 4.2.1.1 activity which catalyzes the conversion between carbon dioxide and bicarbonate [$CO_2$+$H_2O \leftrightarrows HCO_3^- + H^+$]. For purposes of the present invention, CA activity is determined according to the procedure described in Example 4. One unit of CA activity is defined after Wilbur [$1\ U=(1/t_c)-(1/t_u)\times 1000$] where U is units and $t_c$ and $t_u$ represent the time in seconds for the catalyzed and uncatalyzed reaction, respectively (Wilbur, 1948, *J. Biol. Chem.* 176: 147-154). The polypeptides of the present invention are considered to have CA activity if they have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the polypeptide consisting of the amino acid sequence corresponding to amino acid residues 28 to 259 or 36 to 259 of SEQ ID NO: 2.

The terms "$CO_2$-lean" and "$CO_2$-rich" carrier liquid are terms used in the present invention to describe the relative amount of carbon (e.g., in the form of dissolved $CO_2$, chemically reacted $CO_2$, bicarbonate, carbonic acid and/or carbonate salt) present in the carrier liquid as it circulates through the process. As used herein, the term "$CO_2$-lean carrier liquid" generally refers to carrier liquid entering an absorption module. The term "$CO_2$-rich carrier liquid" generally refers to a carrier liquid entering a desorption module. It is understood that the term "$CO_2$-lean carrier liquid" can also be applied to carrier liquid exiting a desorption module, and the term "$CO_2$-rich carrier liquid" can also be applied to carrier liquid exiting an absorption module. $CO_2$-rich carrier liquid contains more carbon compared to $CO_2$-lean carrier liquid within a system at a given point in time.

The term "$CO_2$-containing medium" is used to describe any material which contains at least 0.001% $CO_2$, preferably at least 0.01%, more preferably at least 0.1%, more preferably at least 1%, more preferably at least 5%, most preferably 10%, even more preferred at least 20%, and even most preferably at least 50% $CO_2$. Preferably the $CO_2$-containing medium has a temperature between 5° C. and 110° C., more preferably between 10° C. and 100° C., more preferably between 20° C. and 95° C., more preferably between 30° C. and 90° C., more preferably between 40° C. and 85° C., more preferably between 50° C. and 80° C., more preferably between 55° C. and 75° C., and most preferably between 60° C. and 70° C. at any pressure. $CO_2$-containing media are in particular gaseous phases (including gas mixtures), liquids or multiphase mixtures, but may also be solid. A $CO_2$-containing gaseous phase is for example raw natural gas obtainable from oil wells, gas wells, and condensate wells, syngas generated by the gasification of a carbon containing fuel (e.g., methane) to a gaseous product comprising CO and $H_2$, or emission streams from combustion processes, e.g., from carbon based electric generation power plants, or from flue gas stacks from such plants, industrial furnaces, stoves, ovens, or fireplaces or from airplane or car exhausts. A $CO_2$-containing gaseous phase may alternatively be ambient air (including hot (above 40° C.) air, e.g., desert air), or from respiratory processes in mammals (such as the $CO_2$-containing gas phase in an artificial lung), living plants and other $CO_2$ emitting species, in particular from green-houses. A $CO_2$-containing gas phase may also be off-gas, from aerobic or anaerobic fermentation, such as brewing, fermentation to produce useful products such as ethanol, or the production of biogas. Such fermentation processes can occur at elevated temperatures if they are facilitated by thermophilic microorganisms, which are for example encountered in the production of biogas. A $CO_2$-containing gaseous phase may alternatively be a gaseous phase enriched in $CO_2$ for the purpose of use or storage. The above described gaseous phases may also occur as multiphase mixtures, where the gas co-exists with a certain degree of fluids (e.g., water or other solvents) and/or solid materials (e.g., ash or other particles). $CO_2$-containing liquids are any solution or fluid, in particular aqueous liquids, containing measurable amounts of $CO_2$, preferably at one of the levels mentioned above at any pressure. $CO_2$-containing liquids may be obtained by passing a $CO_2$-containing gas or solid (e.g., dry ice or soluble carbonate containing salt) into the liquid. $CO_2$-containing fluids may also be compressed $CO_2$ liquid (that contains contaminants, such as dry-cleaning fluid), supercritical $CO_2$, or $CO_2$ solvent liquids, like ionic liquids.

The term "$CO_2$ extraction" is to be understood as a reduction of carbon from a $CO_2$-containing medium. Such an extraction may be performed from one medium to another, e.g., gas to liquid, liquid to gas, gas to liquid to gas, liquid to liquid or liquid to solid, but the extraction may also be the conversion of $CO_2$ to bicarbonate, carbonate or carbonic acid within the same medium or the conversion of bicarbonate to $CO_2$ within the same medium. The term $CO_2$ capture is also used to indicate extraction of $CO_2$ from one medium to another or conversion of $CO_2$ to bicarbonate/carbonate or conversion of bicarbonate/carbonate to $CO_2$.

The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "functional fragment of a polypeptide" or "a polypeptide fragment having carbonic anhydrase activity" is used to describe a polypeptide which is derived from a longer polypeptide (parent polypeptide), e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the parent polypeptide.

The term "identity" is used to describe the relatedness between two amino acid sequences or two nucleic acid sequences. For purposes of the present invention, the alignment of two amino acid sequences is determined by using the Needle program from the EMBOSS package (emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5. The degree of identity between two amino acid sequences is calculated as the number of exact matches in an alignment of the two sequences, divided by the length of the shortest sequence. The result is expressed in percent identity. An exact match occurs when the "first sequence" and the "second sequence" have identical amino acid residues in the same positions of the overlap (in the alignment example below this is represented by "|"). In the purely hypothetical alignment example below, the overlap is the amino acid sequence "HTWGERNL" of Sequence 1; or the amino acid sequence "HGWGEDANL" of Sequence 2. In the example a gap is indicated by a "-"

```
Sequence 1: ACMSHTWGER-NL      (SEQ ID NO: 10)
              | ||| ||
Sequence 2:    HGWGEDANLAMNPS  (SEQ ID NO: 11)
```

The degree of identity between two nucleotide sequences is determined using the same algorithm, software package and settings as described above.

The term "heat-stable" or "thermostable" as used in reference to an enzyme, such as a carbonic anhydrase, indicates that the enzyme is functional or active (i.e., can perform catalysis) at an elevated temperature, i.e., above 45° C., preferably above 50° C., more preferably above 55° C., more preferably above 60° C., even more preferably above 65° C., most preferably above 70° C., most preferably above 75° C., most preferably above 80° C., most preferably above 85° C. most preferably above 90° C., and even most preferably above 100° C. In a preferred embodiment the carbonic anhydrase displays optimum activity at one of the temperatures indicated above, i.e., the enzyme's temperature optimum is at one of the temperatures indicated above. The temperature stability of the carbonic anhydrase can be increased to some extent by way of formulation, e.g., by combination with stabilizing chemicals or by immobilization of the enzyme, or by chemical modification, e.g. cross-linking, to preserve the enzyme in its active three dimensional shape. In order for an enzyme to be considered heat-stable it remains active after at least 15 minutes, preferably for at least 2 hours, more preferably for at least 24 hours, more preferably for at least 7 days, more preferably for at least 10 days, even more preferably for at least 14 days, most preferably for at least 30 days, even most preferably for at least 50 days at the elevated temperature. Generally, the level of activity is measured using the assay described in Example 5 after incubation for the given time in 0.1 M Britton-Robinson buffer at pH 8 at the given elevated temperature. The activity may be compared with the enzyme activity prior to the temperature elevation, thereby obtaining the residual activity of the enzyme after the heat treatment. Preferably, the residual activity is at least 30% after the given time at the elevated temperature, more preferably at least 40%, more preferably at least 50%, more at least 60%, even more preferably at least 70%, most preferably at least 80%, even most preferably the residual activity is at least 90%, and absolutely most preferred the level of residual activity is at least equal to or unchanged after the given time at the elevated temperature.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

The term "mature polypeptide" means a polypeptide in its final form following translation and any post-translational modifications, such as N-terminal processing, C-terminal truncation, glycosylation, phosphorylation, etc. In one aspect, the mature polypeptide is 36 to 259 of SEQ ID NO: 2 or amino acid residues 23 to 243 of SEQ ID NO: 13. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having carbonic anhydrase activity.

The term "operably linked" means a configuration in which a control sequence is placed at an appropriate position relative to the coding sequence of a polynucleotide such that the control sequence directs the expression of the coding sequence.

The term "secreted polypeptide" as used herein is to be understood as a polypeptide which after expression in a cell is either transported to and released to the surrounding extracellular medium or is associated/embedded in the cellular membrane so that at least a part of the polypeptide is exposed to the surrounding extracellular medium.

The term "subsequence" means a polynucleotide having one or more (several) nucleotides deleted from the 5' and/or 3' end of a mature polypeptide coding sequence; wherein the subsequence encodes a fragment having carbonic anhydrase activity The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form".

The term "syngas" or "synthesis gas" is used to describe a gas mixture that contains varying amounts of carbon monoxide and hydrogen generated by the gasification of a carbon containing fuel (e.g., methane or natural gas) to a gaseous product with a heating value. $CO_2$ is produced in the syngas reaction and must be removed to increase the heating value.

The term "thermophilic" in relation to an organism, describes an organism which thrives at relatively high temperatures, i.e., above 45° C. Hyperthermophilic organisms thrive in extremely hot environments, that is, hotter than around 60° C. with an optimal temperature above 80° C.

Carbonic Anhydrases Obtainable from *Caminibacter* and their Use

Currently, a few heat-stable carbonic anhydrase are known, including the beta-class CA (Cab) from *Methanobacterium thermoautotrophicum* ΔH, which has been reported to be heat stable to up to 75° C. (Smith and Ferry, 1999, *J. Bacteriol.* 181: 6247-6253) and the gamma-class carbonic anhydrase (Cam) from *Methanosarcina thermophila* TM-1. Cam was isolated for the first time in 1994 (Alber and Ferry, 1994, *Proc. Natl. Acad. Sci. USA* 91: 6909-1913), and in 1996 it was shown to be stable to heating at 55° C. for 15 min (Alber and Ferry, 1996, *J. Bacteriol.* 178: 3270-3274). Cam is the only isolated enzyme of the gamma-class, and has been subject to a lot of characterization studies since its discovery. US 2006/0257990 describes variants of human carbonic anhydrase II where the most stable variant shows activity up to 65° C. US 2004/0259231 discloses the use of Cab as well as the non-thermostable human CA isoform IV in a $CO_2$ solubilization and concentration process. WO 2008/095057 describes heat-stable alpha-carbonic anhydrases from *Bacillus clausii* and *Bacillus halodurans* and their use for the extraction of $CO_2$.

One aspect of the present invention is the technical application of heat-stable carbonic anhydrase isolated from bacteria strains of the genus *Caminibacter*, or carbonic anhydrase which falls within the given sequence identity of the *Caminibacter* carbonic anhydrases of the invention, in the extraction of $CO_2$ from a $CO_2$-containing medium, such as a gas, a liquid, or multiphase mixture. Preferably the *Caminibacter* carbonic anhydrase is an alpha-class carbonic anhydrase. Preferably, the $CO_2$ is extracted from one medium, such as a gas, to a second medium such as a liquid involving the conversion of $CO_2$ to bicarbonate within the second medium, this is also termed absorption of $CO_2$. The reverse extraction process where bicarbonate in the $CO_2$-containing medium is converted to $CO_2$ which can then be released from the first medium to a second medium, such as a gas, is also a desirable process where the carbonic anhydrase of the present invention can be applied. This process is also termed desorption of $CO_2$. The present invention is in particular useful where the temperature of the $CO_2$-containing medium and/or the temperature of certain stages of the extraction process where carbonic anhydrase is present is above the temperature optimum for commercially available carbonic anhydrases, such as CA-I or CA-II isolated from human or bovine erythrocytes, which have temperature optimums at approximately 37° C., or where the temperature is above the temperature optimum of the few known thermostable carbonic anhydrases. One example of a process stage where elevated temperatures may occur is when the hot flue gas is brought into contact with the carbonic anhydrase containing liquid used to absorb the $CO_2$ from the flue gas. Another example is the current $CO_2$ scrubbing technologies, such as chemical absorption with carbonates (e.g., hot potassium carbonate process), alkanolamines (e.g., monoethanolamine, methyldiethanolamine, etc.) or other amines (e.g., ammonia), which use elevated temperatures (up to about 120 to 130° C.) in the desorption process.

Several bacterial strains belonging to the genus *Caminibacter* have been isolated from deep-sea hydrothermal vents. Currently, three species have been identified, namely *C. hydrogeniphilus, C. mediatlanticus* and *C. profundus* (Alain et al., 2002, *International Journal of Systematic and Evolutionary Microbiology* 52: 1317-23; Miroshnichenko et al., 2004, *International Journal of Systematic and Evolutionary Microbiology* 54: 41-45 and Voordeckers et al., 2005, *International Journal of Systematic and Evolutionary Microbiology* 55: 773-79). The strains have been reported to grow at temperatures between 45° C. and 70° C. *Caminibacter mediatlanticus* TB-2 has been subjected to genomic sequencing (EMBL-EBI ID ABCJ01000003). The open reading frame identified as SEQ ID NO: 1 in the present application was obtained from this work, and it was predicted that the translated polypeptide sequence published with UniProt accession nr. A6DCH2 may give rise to a protein with carbonic anhydrase activity. It appears that the protein has never been expressed or characterized to confirm this prediction. The examples of the present invention describe, for the first time, the cloning, expression and isolation of the mature carbonic anhydrase from *C. mediatlanticus* DSM 16658 and confirm that the amino acid sequence gives rise to an enzyme with carbonic anhydrase activity. The characterization of the enzyme also revealed that it is thermostable to a level which could not have been expected based on the growth temperature of the bacterium. It was shown that the enzyme maintained all its carbonic anhydrase activity after incubation in 1 M $NaHCO_3$ at pH 8 or 0.1 M Britton-Robinson buffer pH 8 at 80° C. for 15 minutes and after 2 hours the residual activity was 83% or 82%, respectively.

The carbonic anhydrase which is most closely related to the *Caminibacter* carbonic anhydrase with UniProt accession nr: A6DCH2, is *Nitratiruptor* sp. carbonate dehydratase (EC=4.2.1.1, UNIPROT accession nr: A6Q1X3) which is 52.9% identical. The present invention furthermore discloses a novel carbonic anhydrase isolated from *Caminibacter hydrogeniphilus* DSM 14510. This carbonic anhydrase is 58.2% identical to the mature sequence of the *Caminibacter* carbonic anhydrase with UniProt accession nr: A6DCH2 and 52.8% identical to the *Nitratiruptor* sp. carbonate dehydratase (EC=4.2.1.1, UNIPROT accession nr: A6Q1X3). The open reading frame of the *C. hydrogeniphilus* CA is identified as SEQ ID NO: 12, a synthetic gene optimized for expression in *Bacillus subtitlis* is identified as SEQ ID NO: 16. It is likely that a better expression can be obtained by further optimization of SEQ ID NO: 16. The carbonic anhydrase encoded by these sequences are indicated as SEQ ID NO: 13 and 15. It has been shown that this enzyme is stable for at least 15 min at 80° C.

One embodiment of the present invention is an isolated polypeptide having carbonic anhydrase activity selected from the group consisting of: a) a polypeptide derived from or producible by *Caminibacter hydrogeniphilus* DSM 14510; or b) a polypeptide having an amino acid sequence corresponding to amino acid residues 23 to 243 of SEQ ID NO: 13; or c) a polypeptide which is at least 60%, 65%, 70%, 75%, 80%, 85%, 90%, 91%, 92%, 93%, 94%, 95%, 96%, 97%, 98% or 99% identical to amino acid residues 23 to 243 of SEQ ID NO: 13; or d) a fragment of (a), (b) or (c) having carbonic anhydrase activity; or e) a polypeptide encoded by a nucleic acid sequence which hybridizes under medium stringency conditions with: i) a polynucleotide sequence encoding a mature polypeptide of SEQ ID NO: 13; or ii) a polynucleotide sequence of SEQ ID NO: 12 or SEQ ID NO: 16; or iii) a subsequence of (i) or (ii), of at least 100 contiguous nucleotides, or iv) a complementary strand of (i) or (ii); or f) a polypeptide encoded by a nucleic acid sequence which, because of the degeneracy of the genetic code, does not hybridize with the polynucleotide sequence of SEQ ID NO: 12 or SEQ ID NO: 16, but which codes for a polypeptide having an amino acid sequence according to b) or c) or g) a polypeptide encoded by a nucleic acid sequence which is at least 60%, 65%, 70%, 75%, 80%, 85%, 90%, 95%, 96%, 97%, 98%, 99% or 100% identical to SEQ ID NO: 12 or SEQ ID NO: 16.

In one embodiment of the present invention the carbonic anhydrase to be applied in the extraction of $CO_2$ is derived from, obtainable from or producible by bacteria strains selected from one of the species *Caminibacter hydrogeniphilus, Caminibacter mediatlanticus* or *Caminibacter profundus*, preferably from the carbonic anhydrase to be applied in the extraction of $CO_2$ is derived from or producible by one of the strains deposited as *Caminibacter hydrogeniphilus* DSM 14510, *Caminibacter mediatlanticus* DSM 16658 or *Caminibacter profundus* DSM 15016.

In a further embodiment the carbonic anhydrases to be applied in the extraction of $CO_2$ is a) derived from, obtainable from or producible by *Caminibacter mediatlanticus* DSM 16658 or *Caminibacter hydrogeniphilus* DSM 14510; or b) a polypeptide having an amino acid sequence corresponding to amino acid residues 28 to 259 or 36 to 259 of SEQ ID NO: 2 or amino acid residues 23 to 243 of SEQ ID NO: 13; or c) a polypeptide which is at least 60%, 65%, 70%, 75%, 80%, 85%, 90%, 91%, 92%, 93%, 94%, 95%, 96%, 97%, 98% or 99% identical to amino acid residues 28 to 259 or 36 to 259 of SEQ ID NO: 2 or amino acid residues 23 to 243 of SEQ ID NO: 13; or d) a fragment of (a) or (b) or (c) having carbonic anhydrase activity; or e) a polypeptide encoded by a nucleic acid sequence which hybridizes under medium stringency conditions with: i) a polynucleotide sequence encoding a mature polypeptide of SEQ ID NO: 2 or SEQ ID NO: 13; or ii) a polynucleotide sequence of SEQ ID NO: 1, SEQ ID NO: 12 or SEQ ID NO: 16; or iii) a subsequence of (i) or (ii), of at least 100 contiguous nucleotides, or iv) a complementary strand of (i) or (ii) (Sambrook, Fritsch, and Maniatis, 1989, *Molecular Cloning, A Laboratory Manual,* 2d edition, Cold Spring Harbor, N.Y.), or f) a polypeptide encoded by a nucleic acid sequence which, because of the degeneracy of the genetic code, does not hybridize with the polynucleotide sequence of SEQ ID NO: 1, SEQ ID NO: 12 or SEQ ID NO: 16, but which codes for a polypeptide having an amino acid sequence according to b) or c) or g) a polypeptide encoded by a nucleic acid sequence which is at least 60%, 65%, 70%, 75%, 80%, 85%, 90%, 91%, 92%, 93%, 94%, 95%, 96%, 97%, 98%, 99% or 100% identical to SEQ ID NO: 1, SEQ ID NO: 12 or SEQ ID NO: 16. The polypeptide in c), e) or g) can be synthetic or derived from other species than *Caminibacter* as long as the polypeptide fall within the claimed identities and maintain carbonic anhydrase activity. When the term *Caminibacter* carbonic anhydrase is used it also includes the carbonic anhydrases of c), e) and g.)

In accordance with the present invention hybridization conditions are defined as follows. For long probes of at least 100 nucleotides in length, very low to very high stringency conditions are defined as prehybridization and hybridization at 42° C. in 5×SSPE, 0.3% SDS, 200 micro-g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures. The carrier material is washed once in 6×SCC plus 0.1% SDS for 15 minutes and twice each for 15 minutes using 6×SSC at 5° C. to 10° C. below the calculated $T_m$.

Polypeptide sequences with a given % identity to SEQ ID NO: 2 or SEQ ID NO: 13 or polynucleotide sequences with a given % identity to SEQ ID NO: 1, SEQ ID NO: 12 or SEQ ID NO: 16, may be obtained from naturally occurring sources such as other bacterial strains. Alternatively, the polypeptide or polynucleotide sequences may be obtained by substitution, deletion, and/or insertion of one or more amino acids or nucleic acids in the parent sequence (SEQ ID NO: 1 SEQ ID NO: 12 or SEQ ID NO: 16 for polynucleotides and SEQ ID NO: 2 or SEQ ID NO: 13 for polypeptides). Preferably the number of amino acids which is changed in the parent sequence or the polypeptide encoded by the parent polynucleotide is between 1 to 5, 1 to 10, 1 to 20, 1 to 30 or 1 to 40 amino acids. The amino acid changes are, preferably, of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tag or a polyhistidine-glutamine tag, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., carbonic anhydrase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. A large number of these analyses have already been performed on carbonic anhydrases, the most important are for example reviewed in Tripp et al., 2001, J. Biol. Chem. 276: 48615-48618 and Lindskog, 1997, Pharmacol. Ther. 74: 1-20. The identities of essential amino acids can also be inferred from analysis of identities with polypeptides which are related to a polypeptide according to the invention.

Alpha-carbonic anhydrases are identified by their consensus sequence motif: S-E-[HN]-x-[LIVM]-x(4)-[FYH]-x(2)-E-[LIVMGA]-H-[LIVMFA](2) (SEQ ID NO: 22). The respective consensus residues corresponds to positions 113 to 129 in SEQ ID NO: 13 and in positions 130 to 146 in SEQ ID NO: 2. In a preferred embodiment all consensus positions are present in the carbonic anhydrase.

The following amino acid residues H108, H110, and H127 (numbering according to SEQ ID NO: 13) are predicted to form a histidine triad which is important for catalysis. In a preferred embodiment of the present invention the carbonic anhydrase contains a histidine in position, 108, 110 and 127 (using SEQ ID NO: 13 numbering).

The following amino acid residues H83, E114, Q105 and T145 (using SEQ ID NO: 13 numbering) are predicted to participate in a proton shuttle mechanism, which also is relevant for the catalytic activity of the enzyme (analogous to Human CAII as described by Smith and Ferry, 2000, FEMS Microbiol Rev. 24: 335-366.). In a further embodiment the carbonic anhydrase contains a histidine in position 83 (using SEQ ID NO: 13 numbering) and/or a glutamine in position 106 (using SEQ ID NO: 13 numbering) and/or a glutamic acid in position 114 (using SEQ ID NO: 13 numbering) and/or a threonine in position 195 (using SEQ ID No: 13 numbering). Preferably, at least one of the proton shuttle positions are present, more preferably at least two proton shuttle positions are present, more preferably at least three proton shuttle positions are present and most preferably all the proton shuttle positions are present in the carbonic anhydrase.

The following cysteine residues C45 and C199 are predicted to engage in a cysteine bridge and may therefore be important for the stability of the carbonic anhydrase. Respective cysteine residues were previously identified in Neisseria gonorrhoeae CA (Huang et al, 1998, J Mol Biol, 283: 301-310.). In a preferred embodiment of the present invention the carbonic anhydrase contains a cysteine in position 45 and 199 (using SEQ ID No: 13 numbering).

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The *Caminibacter* carbonic anhydrases described above are useful in a series of applications which are described in more detail below. When referring to *Caminibacter* carbonic anhydrase or carbonic anhydrase below it is intended to include all the carbonic anhydrases described in the present invention in particular if they fall within the claimed identities.

In particular *Caminibacter* carbonic anhydrase may be used for carbon dioxide extraction from $CO_2$ emission streams, e.g., from carbon-based or hydrocarbon-based combustion in electric generation power plants, or from flue gas stacks from such plants, industrial furnaces, stoves, ovens, or fireplaces or from airplane or car exhausts. *Caminibacter* carbonic anhydrases may also be used to remove $CO_2$ in the preparation of industrial gases such as acetylene ($C_2H_2$), carbon monoxide (CO), chlorine ($Cl_2$), hydrogen ($H_2$), methane ($CH_4$), nitrous oxide ($N_2O$), propane ($C_3H_8$), sulfur dioxide ($SO_2$), argon (Ar), nitrogen ($N_2$), and oxygen ($O_2$). *Caminibacter* carbonic anhydrase can also be used to remove $CO_2$ from a raw natural gas during the processing to natural gas. Removal of $CO_2$ from the raw natural gas will serve to enrich the methane ($CH_4$) content in the natural gas, thereby increasing the thermal units/m$^3$. Raw natural gas is generally obtained from oil wells, gas wells, and condensate wells. Natural gas contains between 1% to 10% $CO_2$ when obtained from geological natural gas reservoirs by conventional methods, but depending on the natural source or recovery method used may contain up to 50% $CO_2$ or even higher. Carbonic anhydrase can also be used to purify the natural gas such that it is substantially free of $CO_2$, e.g., such that the $CO_2$ content is below 1%, preferably below 0.5%, 0.2%, 0.1%, 0.05% and most preferably below 0.02%. In resemblance to the methane enrichment of natural gases, carbonic anhydrases can also be used to enrich the methane content in biogases. Biogases will always contain a considerable degree of $CO_2$, since the bacteria used in the fermentation process produce methane (60-70%) and $CO_2$ (30-40%). Biogas production may be performed using mesophilic or thermophilic microorganisms. Thermophilic strains allow the fermentation to occur at elevated temperatures, e.g., from 40° C. to 80° C., and preferably from 50° C. to 70° C. and even more preferably from 55° C. to 60° C. In such processes a heat-stable carbonic anhydrase is particularly useful to remove $CO_2$ from the methane. The present invention provides for the use of a *Caminibacter* carbonic anhydrase to reduce the carbon dioxide content in a biogas, preferably the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Furthermore, carbonic anhydrase may be applied in the production of syngas by removing the $CO_2$ generated by the gasification of a carbon containing fuel (e.g., methane or natural gas) thereby enriching the CO, $H_2$ content of the syngas. Where syngas production occurs at elevated temperatures the use of a heat-stable carbonic anhydrase is an advantage. The present invention provides for the use of a carbonic anhydrase to reduce the carbon dioxide content in a syngas production. Preferably, the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Preferably, the carbonic anhydrases to be used for $CO_2$ extraction as described above maintain residual activity of at least 30%, preferably above 40%, more preferably above 50%, more preferably above 60%, even more preferably above 70%, most preferably above 80%, most preferably above 85%, most preferably above 90%, most preferably above 95%, and even most preferably the residual activity is unchanged after incubation in 0.1 M Britton-Robinson buffer pH 8 at temperatures above 45° C., preferably above 50° C., above 55° C., above 60° C., above 65° C., more preferably above 70° C., most preferably above 80° C., most preferably above 90° C., most preferably above 100° C., most preferably above 105° C. and even most preferably above 110° C. for at least 15 minutes, preferably for at least 2 hours, more preferably for at least 24 hours, more preferably for at least 7 days, more preferably for at least 10 days, even more preferably for at least 14 days, most preferably for at least 30 days, even most preferably for at least 50 days at the elevated temperature. The temperature stability of the carbonic anhydrase can be increased to some extent by formulation, e.g., by immobilization of the enzyme.

In an aspect of the present invention the $CO_2$ extraction from a $CO_2$-containing medium is performed in enzyme based bioreactors. Before the carbon dioxide-containing medium is processed in a bioreactor, it may be purified to free it from contaminants which may disturb the enzymatic reaction or interfere with bioreactor functionality in other ways, e.g., by clotting outlets or membranes. Gasses/multiphase mixtures emitted from combustion processes, e.g., flue gases or exhausts, are preferably cleared of ash, particles, $NO_x$ and/or $SO_2$, before the gas/multiphase mixture is passed into the bioreactor. The raw natural gas from different regions may have different compositions and separation requirements. Preferably, oil, condensate, water and natural gas liquids, if present in the raw natural gas, are removed prior to the extraction of $CO_2$ in an enzyme based bioreactor. The $CO_2$ emitted from combustion processes or present in the raw natural gas may be extracted in the same process as the sulfur removal, or it may be extracted in a completely separate process. If the gas at this point exceeds the temperature optimum of the carbonic anhydrase of the present invention, some degree of cooling may be needed. The temperature to which carbonic anhydrase is exposed during $CO_2$ extraction process whether it is the process temperature in the bioreactor or the feed gas temperature may be between 0° C. and 120° C. Preferably the process temperature is between 45° C. and 110° C., more preferably between 50° C. and 90° C., more preferably between 55° C. and 80° C. even more preferably between 60° C. and 75° C., and most preferably between 65° C. and 70° C.

Reactors and processes for gas separation, including $CO_2$ extraction, are well known in the art and are used commercially for various purposes (A. Kohl and R. Nielsen, Gas Purification, 5$^{th}$ ed. Gulf Professional Publishing, Houston, Tex., 1997). There are several types of reactors which may be combined with the carbonic anhydrase of the present invention to generate a bioreactor (a reactor comprising biological material such as an enzyme) for extracting $CO_2$ from gases, such as combustion gases or respiration gases. Because carbonic anhydrase improves the rate of $CO_2$ extraction, combining carbonic anhydrase with the $CO_2$ extraction reactor enables reactor and process improvements such as smaller size and less expensive absorption modules (e.g., shorter absorption column) and use of low energy consuming and low volatility carrier liquids, as well as overall lower operating temperatures compared to the conventional approaches.

One type of reactor uses liquid membranes. This may for example be reactors including hollow fiber membranes containing a liquid film as described in Majumdar et al., 1988, *AIChE* 34: 1135-1145; U.S. Pat. No. 4,750,918; U.S. Pat. No. 6,156,096; WO 04/104160. Such hollow fiber membrane-based designs are also sometimes termed hollow fiber liquid membranes (HFLM) and the $CO_2$ separation devices based on these have been termed hollow fiber contained liquid membrane (HFCLM) permeators. A common feature of HFCLM permeators is that the hollow fibers enclosing the feed and sweep gas streams are near (i.e., "tightly packed" or "immediately adjacent") to one another and they are enclosed in a single rigid treatment chamber to form one complete permeator. In such a design, a liquid surrounds the shell side of the tightly packed feed and sweep hollow fibers. Because the distance between the outside wall of one hollow fiber is very close to adjacent hollow fibers the thickness of the liquid layer between them is thin, like a membrane, and the composition of the liquid only allows certain components to pass, hence the term "liquid membrane" has been used to describe the liquid surrounding the hollow fibers. Contained liquid membrane permeators where the liquid film is sandwiched between two structural support membranes have also been described in the art (Cowan et al., 2003, *Ann. NY Acad. Sci.* 984: 453-469); this design essentially functions in the same way as the HFCLM. Contained liquid membrane permeators have also been used in combination with carbonic anhydrase as described in U.S. Pat. No. 6,143,556, WO 2004/104160, Cowan et al., 2003, *Ann. NY Acad. Sci.* 984: 453-469; and Trachtenberg et al., 2003, SAE international Conference on Environmental Systems Docket number 2003-01-2499. In these cases, the $CO_2$ desorption step takes place in the same enclosed treatment chamber as the adsorption step. Another example describes an amine based $CO_2$ capture reactor based on absorber/desorber hollow fiber membrane modules (Kosaraju et al., 2005, *Ind. Eng. Chem. Res.* 44:1250-1258).

Another type of reactor uses direct gas-liquid contact. This may for example be conventional solvent based $CO_2$ capture reactors that are based on absorber/desorber column reactors (US 2008/0056972, Reddy et al., *Second National Conference on Carbon Sequestration*, NETL/DOE, Alexandria, Va., May 5-8, 2003). Example flow schemes for commercial direct gas-liquid contactor reactors that use alkanolamines (such as monoethanolamine, diethanolamine, and methyldiethanolamine) for $CO_2$ extraction are shown in A. Kohl and R. Nielsen, Gas Purification, $5^{th}$ ed., Gulf Professional Publishing, Houston, Tex., 1997: 57-62. Example flow schemes for commercial direct gas-liquid contactor reactors that use alkaline salt solutions (such as potassium carbonate) for $CO_2$ extraction are shown in A. Kohl and R. Nielsen, Gas Purification, $5^{th}$ ed., Gulf Professional Publishing, Houston, Tex., 1997: 334-340. Direct gas-liquid contact reactors using carbonic anhydrase have been described in U.S. Pat. No. 6,524,843; WO 2004/007058, WO 2004/056455, U.S. Pat. No. 7,176,017, and US 2004/0059231. In this type of reactor the gas phase or multiphase mixture, is contacted with a liquid phase under conditions where the $CO_2$ in the gas phase is absorbed by the liquid phase where it is converted into bicarbonate by carbonic anhydrase. The bicarbonate enriched liquid is removed from the reactor by a continuous flow, to ensure that the equilibrium between $CO_2$ and bicarbonate is shifted towards continuous conversion of $CO_2$. The gas phase dissolution into the liquid phase is dependent on the surface contact area between the gas and liquid. A large contact area can for example be achieved by passing liquid and $CO_2$-containing gas through a high surface area packed, tray or plate column or tower, by spraying small droplets of liquid through the $CO_2$-containing gas (i.e., a spray contactor), or by bubbling the $CO_2$-containing gas through the liquid (i.e., bubble tank or pond), or by a combination of these techniques. Packed columns can comprise packings such as raschig rings, berl saddles, lessing rings, intalox metal, intalox saddles, pall rings or engineered packings such as Q-PAC (Lantec Products, Inc., Agoura Hills, Calif. 91301). The packing materials may be comprised of a polymer such as nylon, polyester, polyethylene, polyetheretherketone, polypropylene, polystyrene or fluoropolymer (e.g., polytetrafluoroethylene), a ceramic such as silica, or a metal such as aluminium, carbon steel, or stainless steel, or a cellulose-based material such as wood or cotton fiber. In reactor types where the liquid is continuously exchanged or when it is desirable to restrain carbonic anhydrase to one or more locations in the reactor, carbonic anhydrase may be retained in the reactor by various means. In the packed columns the carbonic anhydrase can be immobilized on the packing material (for methods of immobilizing CA, see for example in WO 2005/114417). In the "bubbling" reactors the carbonic anhydrase can be entrapped in a porous substrate, for example, an insoluble gel particle such as silica, alginate, alginate/chitosan, alginate/carboxymethylcellulose, or the carbonic anhydrase can be immobilized (by covalent bonds, ionic charges, entrapment or encapsulation) on a solid packing (as in the packed columns) in suspension in the liquid, or the carbonic anhydrase can be chemically linked in an albumin or PEG network. Carbonic anhydrase can also be restrained to a particular location in the reactor by entrapment in a polymeric immobilization material which may comprise a micellar or inverted micellar material, such as described in WO 2010/037109. Spray contactors may include vertical or horizontal spray chambers, countercurrent spray columns, venturi scrubbers, ejectors or jet scrubbers, cyclone scrubbers, and spray dryers (A. Kohl and R. Nielsen, Gas Purification, $5^{th}$ ed., Gulf Professional Publishing, Houston, Tex., 1997: 418-427 and 604-616). Use of spray contactors is desirable when avoiding pressure drop and tolerance to solid particulates in the gas, such as with atmospheric pressure post-combustion exhaust gas is important. However, to be most effective, the rate of $CO_2$ absorption in spray contactors must be fast, and carbonic anhydrase can provide the needed catalysis to achieve these fast rates.

$CO_2$ extraction in a direct gas-liquid contact reactor may involve a first absorption stage followed by optionally a subsequent desorption, precipitation, utilization, collection, regeneration or release stage. A general description of the absorption stage is as follows. When the absorption reactor is in operation, a water-containing liquid enters the reactor at one end, preferably the top, and flows to the other end, preferably the bottom, and the $CO_2$-containing gas stream (feed gas) enters the reactor at one end, preferably at the opposite end (the bottom) ("countercurrent") from the liquid and the gas passes through the liquid and exits, minus the $CO_2$ extracted into the liquid, through a gas outlet at the opposite end (preferably, the top of the reactor). The liquid that exits the absorption reactor is enriched in bicarbonate/carbonate ($CO_2$-rich liquid) and the exit gas is reduced in the $CO_2$ content compared to the feed gas. The $CO_2$-rich liquid may be processed in subsequent reactions, for example to generate pure $CO_2$ by passing through a desorption reactor, or produce carbonate precipitates such as $CaCO_3$. The $CO_2$-rich liquid from the absorption reactor can also be utilized, e.g., to enhance algae growth, collected, e.g., by pumping the $CO_2$-rich liquid into a contained geological formation, released, e.g., by pumping the $CO_2$-rich liquid into the environment, such as release of bicarbonate liquid into seawater from a submarine life support system, evaporated or desalinated. The $CO_2$-rich liquid containing bicarbonate anion can be used in industrial processes, such as in the manufacturing processes for ammonium carbonate and ammonium bicarbonate, which are useful as fertilizer, or in processes for the removal and neutralization of acid gases such as sulfur dioxide.

The reactors described above may involve only an absorption stage, only a desorption stage or absorption followed by a desorption stage in which carbonic anhydrase may catalyze either the hydration of $CO_2$ to bicarbonate or the dehydration of bicarbonate to $CO_2$ or both. The reactors can be combined with each other where each reactor constitutes a module. For example a liquid membrane reactor can function as absorption module and the direct gas-liquid contact reactor can function as a desorption module or vice versa.

Figure 2:
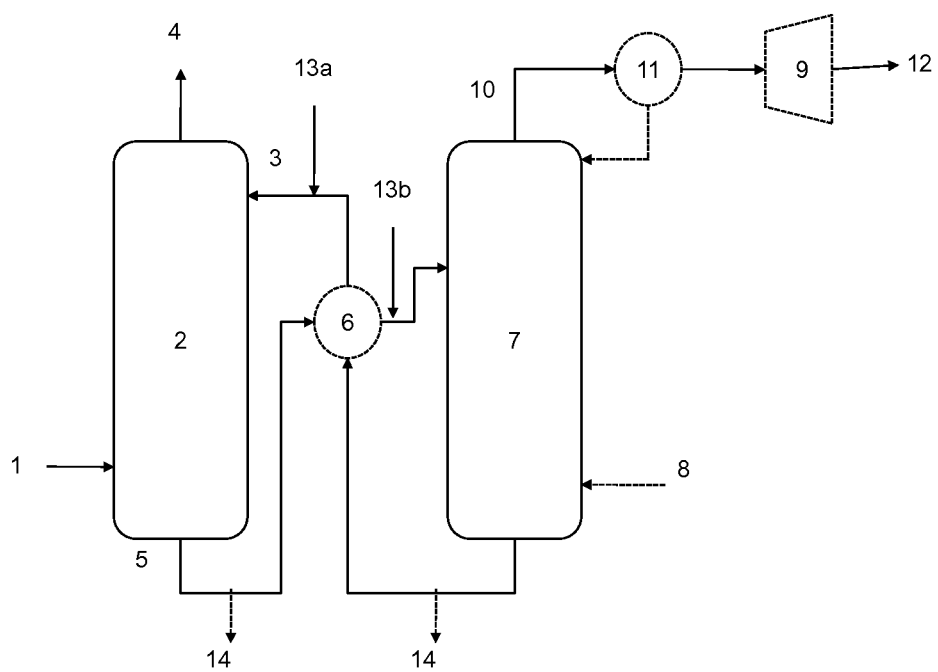
FIG. 2 is a schematic presentation of a general recirculating absorption/desorption process for $CO_2$ extraction from a mixed gas. In the general process, $CO_2$-rich Feed Gas (1) enters the Absorption Module (2) preferably the gas enters one end (e.g., the bottom) where it comes in contact with $CO_2$-Lean Carrier Liquid (3) entering the absorption module, preferably at the opposite end from the feed gas (e.g., the top). Scrubbed Gas (4), from which $CO_2$ has been removed, exits the absorption module. $CO_2$-Rich Carrier Liquid (5) exits the absorption module and (optionally) passes through a Temperature Regulator (e.g., a heat exchanger) (6) before entering (preferably at one end (e.g., the top)) the Desorption Module (7). Heat (8), such as supplied by a re-boiler or direct steam, or Vacuum (9), or a combination of these applied to the desorption module causes extracted $CO_2$ to be released from the carrier liquid and exit (10) the desorption module, (optionally) passing through a Condenser (11) to remove carrier liquid vapor prior to compression and/or use of the Purified $CO_2$ Gas (12). $CO_2$-Lean carrier liquid exits the desorption module and (optionally) passes through a temperature regulator (e.g., heat exchanger) before returning to the absorption module. Depleted and/or auxiliary carrier liquid components can be added at various points in the process, such as at the locations indicated (13a and 13b). Insoluble contaminants can be removed from the circulating liquid at various points in the process, such as at the locations indicated (14).

Without limiting the scope of the present invention, FIG. 2 is provided to illustrate a general schematic of a $CO_2$ extraction reactor comprising both absorption and desorption modules through which the $CO_2$ absorbing carrier liquid circulates as it removes $CO_2$ from a $CO_2$-containing gaseous phase (Feed Gas) in the absorber, releases Purified $CO_2$ Gas in the desorber, then recirculates back to the absorber. The term "Feed gas" is often used in relation to $CO_2$ extraction reactors where it implies that $CO_2$ is removed from the $CO_2$ containing gaseous phase by contact with a $CO_2$-lean carrier liquid in the reactor. The feed gas may be at atmospheric pressure, or at pressures above or below atmospheric pressure. Selective solubility of $CO_2$ in the carrier liquid causes extraction of $CO_2$ from the feed gas into the carrier liquid in the absorber. In the desorber, $CO_2$ is released from the carrier liquid by introducing a pressure difference (for example, a lower partial pressure of $CO_2$ in the desorber gas phase compared to that in the feed gas, such as can be achieved by applying vacuum in the desorber) that lowers the solubility of $CO_2$ in the carrier liquid and/or applying heat, e.g., via a reboiler, steam or a sweep gas to drive $CO_2$ into the gas phase in the desorber. Heat energy alone can be used to drive desorption such as is commonly used in monoethanol amine-based $CO_2$ extraction processes. For example the temperature in the desorber of a typical monoethanol amine-based $CO_2$ extraction is greater than 100° C. (e.g., 120° C.). Alternatively heat energy can be combined with pressure reduction to drive desorption in this case the temperature in the desorber can be lowered. For example, together with a reduced pressure (e.g., vacuum) compared to the pressure in the absorber (e.g., atmospheric pressure), the desorber can be operated at 70° C. A difference in pH can be used to facilitate absorption and desorption, wherein $CO_2$ absorption into an aqueous medium is favored at more alkaline pH whereas $CO_2$ desorption from an aqueous medium is favored at a less alkaline (more acidic) pH. The range of relevant pH difference ("swing") between absorption and desorption depends on the particular process. For example, for the sake of illustration, $CO_2$ absorption into a bicarbonate-based carrier liquid can occur at pH 9 or above resulting in a decrease in the pH of that carrier liquid to below pH 9. Desorption of $CO_2$ from that carrier liquid can then occur at pH below pH 9.

A pressure difference between the absorber and the desorber can be established/occur when the pressure of the feed gas passing through the absorber is higher than the pressure of the gas phase in the desorber. In some cases, such as for natural gas upgrading, the gas pressure in the absorber is higher than in the desorber and the gas pressures in both the absorber and the desorber may be above atmospheric pressure. In other cases, the gas pressure in the absorber is above atmospheric pressure and the gas pressure in the desorber is at or below atmospheric pressure (i.e., equal to or less than 100 kPa). Alternatively, a pressure difference between the absorber and the desorber can be established/occur when the pressure of the feed gas (such as a coal-fired post-combustion flue gas) passing through the absorber is approximately at atmospheric pressure and the pressure of the gas phase in the desorber is below atmospheric pressure. In one embodiment of the present invention, the total gas pressure difference between the absorber and the desorber is at least about 35 kPa.

The absorber and desorber shown schematically in FIG. 2 can be at essentially the same ("isothermal") temperature or at different temperatures. *Caminibacter* carbonic anhydrase may be present in only the absorber or desorber or both. Regeneration of $CO_2$ using vacuum (low pressure) at low temperatures, e.g., 70° C. in the desorber where a high temperature carbonic anhydrase such as *Caminibacter* carbonic anhydrase is present is a further embodiment of the present invention. Carbonic anhydrase in such process catalyzes both absorption and desorption of $CO_2$ to and from absorption solvent. When the absorber and desorber are at different temperatures, a temperature regulator (e.g., heat exchanger) can be used to conserve energy in the process.

In a further illustration, a modification of the vacuum carbonate process for $H_2S$ absorption (A. Kohl and R. Nielsen, Gas Purification, 5$^{th}$ ed., Gulf Professional Publishing, Houston, Tex., 1997, 383-388) has been described for $CO_2$ extraction (US 2007/0256559) and disclosed in combination with carbonic anhydrase (Lu et al., DOE Project No. DE-FC26-08NT0005498, NETL CO2 Capture Technology for Existing Plants R&D Meeting, Mar. 24-26, 2009, Pittsburgh, Pa.). In this illustration, atmospheric pressure power plant flue gas contacts aqueous potassium carbonate and carbonic anhydrase in the absorber column at temperatures in the range 40 to 60° C., where carbonic anhydrase is said to improve the rate of $CO_2$ hydration to bicarbonate in the carrier liquid. The $CO_2$-rich carrier liquid is pumped to a desorber column ("stripper") where $CO_2$ is released from the carrier liquid by a combination of low pressure (e.g., 14-55 KPa) and the application of heat (e.g., 50-70° C.) obtained by directly injecting low pressure, low quality exhaust steam from a low pressure steam turbine of the power plant. Carbonic anhydrase from *Caminibacter* of the present invention is especially suitable for use in the described modified vacuum carbonate process because *Caminibacter* carbonic anhydrase can tolerate temperatures both in the absorber and the desorber, meaning that, unlike other known carbonic anhydrases that would be inactivated by the temperature in the desorber, *Caminibacter* carbonic anhydrase could tolerate the temperature in the desorber, allowing it to circulate along with the carrier liquid through both absorption and desorption stages of the process. Physical agitation, including ultrasonic agitation, can be combined with vacuum to enhance release of $CO_2$ from the carrier liquid in the desorber.

A further type of reactor uses membranes in combination with $CO_2$ hydration catalysis by carbonic anhydrase followed by precipitation. In one case, $CO_2$ is removed from a gaseous stream by passing the gaseous stream through a gas diffusion membrane into solution where conversion to is accelerated by passing the $CO_2$ solution over a matrix that contains carbonic anhydrase and adding a mineral ion to cause precipitation of the carbonic acid salt (U.S. Pat. No. 7,132,090). It has been shown further that carbonic anhydrase not only can catalyze the $CO_2$ hydration/dehydration reaction but also can promote the precipitation of calcium carbonate (Mirjafari et al., 2007, Ind. Eng. Che. Res. 46: 921-926).

A further type of reactor removes $CO_2$ from ambient air. A reactor designed to remove $CO_2$ from ambient air have been reported (Stolaroff et al., 2008, Environ. Sci. Technol. 42: 2728-2735), however this reactor does not utilize carbonic anhydrase. Without being bound by the design of the reported ambient air reactor, a carbonic anhydrase combined with suitable carrier liquids as disclosed in the present invention, could be used in such a reactor or in other reactor designs as described herein. A heat stable carbonic anhydrase is especially useful because exposure of the reactor to environmental conditions, such as sunlight, may increase the liquid temperature beyond the tolerance of known carbonic anhydrases, and avoids the need to cool the reactor. This illustrates a situation where the process of extracting $CO_2$ from the $CO_2$-containing medium may require carbonic anhydrase to function at or tolerate higher temperatures than the initial temperature of the $CO_2$-containing medium, such as ambient air, which may be cold at night (below 10° C.) and hot during the day (above 45° C.).

The different membrane reactors and direct gas-liquid contact reactors described above as well as other alternatives may be applied in a carbon dioxide extraction process, where the absorption process and desorption process occur in at least two steps. Such reactors generally comprise the following elements: a) at least one absorption module, which may comprise a gas inlet zone and/or a gas outlet zone; b) at least one desorption module comprising a gas outlet zone; c) a carrier liquid; and d) means for connecting the absorption module(s) and the desorption module(s) such that the carrier liquid can pass from the absorption module(s) to the desorption module(s). Optionally the means for connecting the absorption and desorption modules is a circuit, allowing the carrier liquid to be returned to the absorption module once it has passed through the desorption module. One or both of the modules may comprise at least one $CO_2$-permeable membrane which separates a gas phase from a liquid phase, such as described in WO 2010/014773 and WO 2010/014774. This module type is also termed a gas-liquid membrane (GLM) module. The GLM module may, e.g., be in the form of a hollow fiber membrane, a flat sheet membrane or a spiral-wound membrane. The GLM module may either function as an absorber module and/or a desorber module. Alternatively, one of the modules may be a GLM module and the other module may be composed such that the gas and liquid phases are in direct contact or in other words the gas-liquid interface is not separated by a membrane. This module type is also termed a direct gas-liquid contact (DGLC) module or just a direct contact (DC) module. The DGLC module may, e.g., be in the form of a column filled with packing material that allows for gas-liquid contact, and/or a liquid-containing vessel equipped with an inlet for exposing gas to the liquid (such as a bubble column), and/or a liquid-spray (such as a spray tower) and/or an aerator module and/or a falling film. The DGLC module may either function as an absorber module or a desorber module. Bubble cap system, sieve plate system, disk-and-doughnut column and packed column are examples of direct gas-liquid contact modules (DGLC).

The reactor types described above may be operated at any desired temperature. In one embodiment, the reactor is operated with a temperature of the liquid in contact with and/or containing carbonic anhydrase between 0° C. and 120° C. or 5° C. and 110° C., more preferably between 10° C. and 100° C., more preferably between 20° C. and 95° C., more preferably between 30° C. and 90° C., more preferably between 40° C. and 85° C., more preferably between 50° C., and 80° C., more preferably between 55° C. and 75° C., and most preferably between 60° C. and 70° C.

The absorption and desorption rates of $CO_2$ are dependent on the pH in the carrier liquid. In the reactor types described in relation to the present invention the pH of the $CO_2$-lean carrier liquid is between pH 4 to 12, preferably above pH 7 (as measured at room temperature, e.g., 20-25° C.), more preferably above pH 8, more preferably between 8 and 12, more preferably between 8 and 10.5, more preferably between 8.5 and 10, even more preferably between 9 and 9.5. Due to the hydration of $CO_2$ to carbonic acid (which immediately dissociates in water to bicarbonate) during absorption, the pH of the carrier liquid decreases as the carbon content of the $CO_2$-rich carrier liquid increases. The extent of pH decrease depends on the buffering capacity of the carrier liquid and the amount of $CO_2$ absorbed. In a preferred embodiment of the present invention the carrier liquid is a bicarbonate buffer, such as sodium bicarbonate, potassium bicarbonate, cesium bicarbonate or another suitable salt of the bicarbonate where depending on the pH greater or lesser amount of carbonate and/or carbonic acid will exsist together with bicarbonate.

In one embodiment of the present invention, the $CO_2$-rich carrier liquid passes through a desorption stage where the pH of the $CO_2$-rich carrier liquid will increase as the $CO_2$ is released. In order to recirculate carrier liquid through such an absorption-desorption system, it is preferred that the pH of the carrier liquid returns to the pH of the $CO_2$-lean carrier liquid before again passing through the absorption stage.

In a preferred embodiment of the present invention the reactor is equipped with means for regulating pH in the carrier liquid. This can be performed in several ways. One way is to add an alkaline substance to the carrier liquid, e.g., at one of the auxiliary components addition points (13a) indicated in FIG. 2, using automatic pH adjustment equipment such as an automatic titrator. The alkaline substance preferably has a similar composition (e.g., concentration of solvent, ionic strength, amount of carbonic anhydrase, etc.) as the carrier liquid circulating in the system and can be added at any time before absorption for adjustment of pH. Similarly a neutral to acidic substance can be added to the carrier liquid any time before desorption, e.g., at one of the auxiliary components addition points (13b) indicated in FIG. 2. Extra carrier liquid can be removed from the system if needed, e.g., at one of the removal points (14) indicated in FIG. 2.

In the $CO_2$ capture processes described above the *Caminibacter* carbonic anhydrase of the present invention may be combined with one or more other carbonic anhydrases. The different process steps in the whole $CO_2$ capture process may require different operating conditions, e.g., temperature, pH, carrier liquid compositions, pressure and so forth. The carbonic anhydrases of the present invention may be combined with other carbonic anhydrases operating at different optimal conditions which are needed in the $CO_2$ capture process. For example, one carbonic anhydrase could circulate in the carrier liquid and a different carbonic anhydrase could be immobilized at one or more locations in the reactor.

The carbonic anhydrase of the present invention or enzyme based bioreactors described above comprising a carbonic anhydrase of the present invention, also find more unconventional applications such as in pilot cockpits, submarine vessels, aquatic gear, safety and firefighting gear and astronaut's space suits and artificial lung devices to keep breathing air free of toxic $CO_2$ levels. Other applications are to remove $CO_2$ from confined spaces, such as to reduce hazardous $CO_2$ levels from inside breweries and enclosed buildings carrying out fermentation, and from $CO_2$ sensitive environments like museums and libraries, to prevent excessive $CO_2$ from causing acid damage to books and artwork. A further alternative application is to remove $CO_2$ from hot ambient air, e.g., in a desert. In this case the carbonic anhydrase could for example be comprised in a reactor suitable for extracting $CO_2$ from ambient air as described in Stolaroff et al., 2008, *Environ. Sci. Technol.* 42: 2728-2735, such a reactor could for example take the form of an "artificial tree".

*Caminibacter* carbonic anhydrase can be used as an independent CO$_2$ extraction catalyst or it may alternatively be combined with conventional CO$_2$ extraction technologies such as chemical absorption via amine-based solvents or aqueous ammonia or physical solvents such as Selexol™ (Union Carbide) or polyethylene glycol ethers. In a further embodiment of the present invention a *Caminibacter* carbonic anhydrase is combined with a carbon dioxide absorbing compound such as amine-based compounds for example aqueous alkanolamines including monoethanolamine (MEA), diethanolamine (DEA), methyldiethanolamine (MDEA), 2-amino-2-hydroxymethyl-1,3-propanediol (Tris), diglycolamine (DGA), 2-amino-2-methyl-1-propanol (AMP), 2-amino-2-hydroxymethyl-1,3-propanediol (AHPD), diisopropanol amine (DIPA), aqueous soluble salts of N-methylaminopropionic acid or other natural or modified amino acids, 2-(2-aminoethylamino)ethanol (AEE), triethanolamine (TEA) or other primary, secondary, tertiary or hindered amine-based solvents including those described on pages 7 to 9 of U.S. Pat. No. 4,112,052 (hereby incorporated by reference), or aqueous salts of glycine and taurine or other liquid absorbers such as aqueous NaOH, KOH, LiOH, carbonate or bicarbonate solutions at different ionic strengths or aqueous electrolyte solutions and promoters such as piperazine, or polyethylene glycol ethers, or a blend of them or analogs or blends thereof. The combination may either be applied in the bioreactors described above or it may be applied to already existing CO$_2$ scrubbing facilities based on conventional techniques. In conventional bioreactors, the concentration of alkanolamines is typically 15-30 weight percent. In an embodiment of the present invention the concentration of alkanolamines could be in the conventional range or preferably at a lower concentration such as preferably below 15% (V/V), more preferably below 12%, 10%, 8%, 6%, 5%, 4%, 3%, 2%, 1%, 0.5%, 0.2% and most preferably below 0.1% (V/V).

In conventional processes, corrosion and oxidation inhibitors, such as contained in Fluor Daniel's proprietary Econ-Amine FG solvent, are added to provide for increasing the amine concentration while reducing the risk of corrosion. Inorganic corrosion inhibitors include vanadium (e.g., sodium metavanadate), antimony, copper, cobalt, tin, and sufur compounds. Organic corrosion inhibitors include thiourea and salicylic acid.

Other auxiliary carrier liquid components can include wetting agents, chelating agents and viscosity reducers, and other compounds capable of increasing the flux of CO$_2$ into or out of the carrier liquid.

In conventional processes, techniques to reduce and/or avoid foam formation are commonly employed. These include removal of foam-causing impurities prior to CO$_2$ extraction and use of antifoaming agents and foam inhibitors such as silicone compounds or high-boiling alcohols such as oleyl alcohol or octylphenoxyethanol (A. Kohl and R. Nielsen, Gas Purification, 5$^{th}$ ed., Gulf Professional Publishing, Houston, Tex., 1997: 224-230).

Another aspect of the present invention relates to biogas production where the CO$_2$ extraction is performed directly in the biogas fermentation broth, as an alternative to passing the biogas through a bioreactor as described above. By adding *Caminibacter* carbonic anhydrase to the anaerobic broth, more CO$_2$ from the gas phase can be converted into bicarbonate, which is the substrate for methane production by the methanogenic Archaea. Particularly, the genus *Methanosarcina* is frequently present in thermophilic biogas digesters (Mladenovska and Ahring, 2000, *FEMS Microbiol. Ecol.* 3: 225-229). It has been shown for *Methanosarcina thermophila* TM-1 that bicarbonate may be a limiting factor for the methane production, for example cultures of *M. thermophila* TM-1 grown in low bicarbonate solution (0.6 mM) showed a considerable lag phase (i.e., methane production began later) when compared with cultures containing ten times higher bicarbonate dosages (6 mM). Additionally, the total yield of methane was 25 times less at the lower bicarbonate dosage (Murray and Zinder, 1985, *Appl. Environ. Microbiol.* 50: 49-55). Consequently, a heat-stable carbonic anhydrase will be particularly useful if the biogas production is performed at elevated temperatures using one or more thermophilic microorganisms, for example methanogens like *Methanosarcina* sp. that can use CO$_2$/biocarbonate as carbon source for growth and methanogenesis.

A further embodiment of the present invention is use of a *Caminibacter* carbonic anhydrase of the present invention as an additive in a biogas fermentation broth.

A further embodiment of the present invention is use of a *Caminibacter* carbonic anhydrase to enhance growth of algae and other aquatic plants that utilize bicarbonate as a carbon source by catalyzing the conversion of CO$_2$ to bicarbonate in or for delivery to the aquatic plant environment. This approach can, for example, be used to simultaneously remove CO$_2$ from a combustion exhaust gas, such as a flue gas, and provide CO$_2$ for conversion to bicarbonate by contacting the exhaust gas with liquid from a cultivation pond. Certain approaches to cultivating algae and aquatic plants involve use of enclosed tubes or shallow troughs or ponds in which heat from sunlight raises the water temperature. Hence a heat stable carbonic anhydrase is particularly useful at the elevated cultivation temperatures.

Polynucleotides

The present invention also relates to isolated polynucleotides encode a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Caminibacter*, or another or related organism and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 12 or SEQ ID NO: 16 of at least 60%, e.g., at least 65%, at least 70%, at least 75%, at least 80%, at least 85%, at least 90%, at least 95%, at least 96%, at least 97%, at least 98%, at least 99%, or 100%, which encode a polypeptide having carbonic anhydrase activity.

The present invention also relates to isolated polynucleotides encoding polypeptides of the present invention, which hybridize under, low stringency conditions, medium stringency conditions, medium-high stringency conditions, high stringency conditions, or very high stringency conditions with (i) a polynucleotide sequence encoding a mature polypeptide of SEQ ID NO: 13, ii) the mature polypeptide coding sequence of SEQ ID NO: 12 or SEQ ID No: 16, or (iii) a subsequence of (i) or (ii), of at least 100 contiguous nucleotides, or iv) a complementary strand of (i) or (ii) the full-length complementary strand of (i) or (ii); or allelic variants and subsequences thereof (Sambrook et al., 1989, supra), as defined herein. The present invention also relates to isolated polynucleotides comprising or consisting of a nucleic acid sequence which, because of the degeneracy of the genetic code, does not hybridize with the polynucleotide sequence of SEQ ID NO: 12 or SEQ ID NO: 16, but which codes for a polypeptide having an amino acid sequence according to b) or c)

In one aspect, the polynucleotide comprises or consists of SEQ ID NO: 12 or SEQ ID NO: 16, the mature polypeptide coding sequence of SEQ ID NO: 12 or SEQ ID NO: 16, or a subsequence of SEQ ID NO: 12 or SEQ ID NO: 16 that encode a fragment of SEQ ID NO: 13 having carbonic anhydrase activity.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a Bacillus cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a Streptomyces cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a Pseudomonas cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Caminibacter*. In a more preferred aspect, the cell is *Caminibacter hydrogeniphilus, Caminibacter mediatlanticus* or *Caminibacter profundus*. In a most preferred aspect, the cell is *Caminibacter hydrogeniphilus* DSM 14510, *Caminibacter mediatlanticus* DSM 16658 or *Caminibacter profundus* DSM 15016.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Compositions Comprising Polypeptides and Methods for their Preparation

The invention provides a composition comprising a *Caminibacter* carbonic anhydrase of the present invention and preferably an excipient and a method for preparing such a composition comprising admixing the polypeptide of the invention with an excipient.

In a particular embodiment the *Caminibacter* carbonic anhydrase of the invention is the major (polypeptide) component of the composition, e.g., a mono-component composition. The excipient in this context is to be understood as any auxilliary agent or compound used to formulate the composition and includes solvent (e.g., water, inorganic salts, fillers, pigments, waxes), carriers, stabilizers, cross-linking agents, adhesives, preservatives, buffers and the like.

The composition may further comprise one or more additional enzymes, such as one or more additional carbonic anhydrases, a decarboxylase, laccase, or oxidase.

The compositions may be prepared in accordance with methods known in the art and may be in the form of a liquid or a solid composition. For instance, the enzyme composition may be formulated using methods known to the art of formulating technical enzymes and/or pharmaceutical products, e.g., into coated or uncoated granules or micro-granules. The polypeptide of the invention may thus be provided in the form of a granule, preferably a non-dusting granule, a liquid, in particular a stabilized liquid, a slurry or a protected polypeptide.

For certain applications, immobilization of the polypeptide may be preferred. An immobilized enzyme comprises two essential functions, namely the non-catalytic functions that are designed to aid separation (e.g., isolation of catalysts from the application environment, reuse of the catalysts and control of the process) and the catalytic functions that are designed to convert the target compounds (or substrates) within the time and space desired (Cao, Carrier-bound Immobilized Enzymes: Principles, Applications and Design, Wiley-VCH Verlag GmbH & Co. KGaA, Weinheim, Germany, 2005). When an enzyme is immobilized it is made insoluble to the target compounds (e.g., substrates) it aids converting and to the solvents used. An immobilized enzyme product can be separated from the application environment in order to facilitate its reuse, or to reduce the amount of enzyme needed, or to use the enzyme in a process where substrate is continuously delivered and product is continuously removed from proximity to the enzyme, which, e.g., reduces enzyme cost. Furthermore, enzymes are often stabilized by immobilization. A process involving immobilized enzymes is often continuous, which facilitates easy process control. The immobilized enzyme can be retained as a heterogeneous catalyst by mechanical means, or by inclusion in a definite space. The latter can be done by microencapsulation, e.g., in semi permeable membranes or by inclusion in UF systems using, e.g., hollow fiber modules, etc. Immobilization on porous carriers is also commonly used. This includes binding of the enzyme to the carrier, e.g., by adsorption, complex/ionic/covalent binding, or just simple absorption of soluble enzyme on the carrier and subsequent removal of solvent. Cross-linking of the enzyme can also be used as a means of immobilization. Immobilization of enzyme by inclusion into a carrier is also industrially applied. (Buchholz et al., Biocatalysts and Enzyme Technology, Wiley-VCH Verlag GmbH & Co. KGaA, Weinheim, Germany, 2005). Specific methods of immobilizing enzymes such as carbonic anhydrase include, but are not limited to, spraying of the enzyme together with a liquid medium comprising a polyfunctional amine and a liquid medium comprising a cross-linking agent onto a particulate porous carrier as described in WO 2007/036235 (hereby incorporated by reference), linking of carbonic anhydrase with a cross-linking agent (e.g., glutaraldehyde) to an ovalbumin layer which in turn adhere to an adhesive layer on a polymeric support as described in WO 2005/114417 (hereby incorporated by reference), or coupling of carbonic anhydrase to a silica carrier as described in U.S. Pat. No. 5,776,741 or to a silane, or a CNBr activated carrier surface such as glass, or co-polymerization of carbonic anhydrase with methacrylate on polymer beads as described in Bhattacharya et al., 2003, *Biotechnol. Appl. Biochem.* 38: 111-117 (hereby incorporated by reference), using globular protein and adhesive as described in US 2010/068784. The carbonic anhydrase may also be immobilized using tags such as histidine-like tags (e.g., 6× His tag or HQ tag) or a cellulose binding module (CBM) (Liu et al., 2008, *Biotechnol. Prog.* 25: 68-74).

An embodiment of the present invention is a composition comprising a matrix suitable for immobilization and a carbonic anhydrase selected from the group consisting of
- a) a polypeptide derived from or producible by *Caminibacter mediatlanticus* DSM 16658 or *Caminibacter hydrogeniphilus* DSM 14510; or
- b) a polypeptide having an amino acid sequence corresponding to amino acid residues 28 to 259 or 36 to 259 of SEQ ID NO: 2 or amino acid residues 23 to 243 of SEQ ID NO: 13; or
- c) a polypeptide which is at least 60% identical to amino acid residues 28 to 259 or 36 to 259 of SEQ ID NO: 2 or to amino acid residues 23 to 243 of SEQ ID NO: 13; or
- d) a fragment of (a), (b) or (c) having carbonic anhydrase activity; or
- e) a polypeptide encoded by a nucleic acid sequence which hybridizes under medium stringency conditions with:
  - i) a polynucleotide sequence encoding a mature polypeptide of SEQ ID NO: 2 or SEQ ID NO: 13; or
  - ii) a polynucleotide sequence of SEQ ID NO: 1 or SEQ ID NO: 12 or SEQ ID NO: 16; or
  - iii) a subsequence of (i) or (ii), of at least 100 contiguous nucleotides, or
  - iv) a complementary strand of (i) or (ii); or
- f) a polypeptide encoded by a nucleic acid sequence which, because of the degeneracy of the genetic code, does not hybridize with the polynucleotide sequence of SEQ ID NO: 1, SEQ ID NO: 12 or SEQ ID NO: 16, but which codes for a polypeptide having an amino acid sequence according to b) or c).

In a further embodiment of the present invention the carbonic anhydrase is immobilized on a matrix. The matrix may for example be selected from the group beads, fabrics, fibers, hollow fibers, membranes, particulates, porous surfaces, rods, structured packing, and tubes. Specific examples of suitable matrices include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, precipitated silica, and TEFLON-brand PTFE. In an embodiment of the present invention carbonic anhydrase is immobilized on a nylon matrix according to the techniques described in Methods in Enzymology volume XLIV (section in the chapter: Immobilized Enzymes, pages 118-134, edited by Klaus Mosbach, Academic Press, New York, 1976), hereby incorporated by reference. The polypeptide to be included in the composition may be stabilized in accordance with methods known in the art, e.g., by stabilizing the polypeptide in the composition by adding an antioxidant or reducing agent to limit oxidation of the polypeptide or it may be stabilized by adding polymers such as PVP, PVA, PEG, sugars, oligomers, polysaccharides or other suitable polymers known to be beneficial to the stability of polypeptides in solid or liquid compositions or it may be stabilized by adding stabilizing ions, such as zinc (e.g., zinc chloride or zinc sulphate) which is present in the enzyme active site. A preservative, such as Proxel, penicillin, can be added to extend shelf life or performance in application.

In embodiments of the present invention the carbonic anhydrase is immobilized by adsorption onto a matrix, surface or substrate. Non-limiting examples of a matrix, surface or substrate include those from the group: beads, fabrics, fibers, hollow fibers, membranes, particulates, porous surfaces, rods, structured packing, and tubes. Specific examples of suitable matrices, surfaces or substrates include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, precipitated silica, and TEFLON-brand PTFE. In embodiments, the matrices, surfaces or substrates may be dried after adsorption of the enzyme.

In a further embodiment the composition of the invention is a composition applicable in the capture of carbon dioxide.

EXAMPLES

Example 1

Cloning and Expression of *Caminibacter mediatlanticus* DSM 16658 Carbonic Anhydrase in *B. subtilis*

A synthetic gene based on the protein sequence of *Caminibacter mediatlanticus* DSM 16658 CA (Uniprot: A6DCH2) was designed and the gene was codon optimized for *B. subtilis*.

The synthetic gene was PCR amplified from the plasmid carrying the synthetic gene. A first PCR reaction (PCR(1)) was performed in a total volume of 50 microliters, the following reagents were added, 1 microliter of synthetic DNA preparation (template), 10 pmol of each of the primers (C1297synthf and C1297synthr), dNTPs and Phusion® polymerase (Finnzymes, Finland) in Phusion GC buffer. The PCR conditions were 94° C. for 2 min; 9 cycles of 94° C. for 15 sec; 55° C. for 45 sec; 68° C. for 1 min; followed by 68° C. for 10 min; 4° C. for 15° C. until the end of the PCR program.

The primers used were:

```
C1297synthf
                                    (SEQ ID NO: 4)
tttagttcatcgatcgcatcggctgcgtcttcttacaactaccacgc C1297synthr
                                    (SEQ ID NO: 5)
gccaaggccggttttttatgttttacttaaggattacgcgagcattg
```

The PCR(1) product had an approximate length of 700 bp and the PCR product was purified. The PCR products were suitable for a subsequent SOE PCR(2) fusion reaction. The signal peptide from the alkaline protease from *B. clausii* (aprH) was fused by SOE fusion as described in WO 99/43835 (hereby incorporated by reference) in frame to the DNA encoding the carbonic anhydrase that was obtained in PCR(1). The nucleotide fragment obtained from PCR(2) containing the carbonic anhydrase coding sequence was integrated by homologous recombination into the Bacillus subtilis host cell genome. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315).

Chloramphenicol resistant transformants were analyzed by DNA sequencing to verify the correct DNA sequence of the construct. The translated protein sequence corresponds to SEQ ID NO: 2, where amino acid 1-17 corresponds to the *B. clausii* aprH signal peptide, amino acids 28-35 is a part of the signal peptide of CA from *C. mediatlanicus* and amino acids 36-259 corresponds to the predicted mature CA.

One expression clone was selected and was cultivated on a rotary shaking table in 500 mL baffled Erlenmeyer flasks each containing 100 ml casein based media supplemented with 34 mg/l chloramphenicol. The clone was cultivated for 4 days at 37° C. It was determined that there was carbonic anhydrase activity in the culture broth according to Wilbur, 1948, *J. Biol. Chem.* 176: 147-154 (essentially as described in Example 5).

Example 2

Cloning and Expression of *Caminibacter mediatlanticus* DSM 16658 Carbonic Anhydrase with N-terminal HQ Tag and Thrombin Cleavage Site in *B. subtilis*

The plasmid containing the synthetic gene described in Example 1 was used as a template for PCR(3). The forward primer was CamiHQ coding for an HQ affinity tag.

```
CamiHQ
                                        (SEQ ID NO: 6)
catcagcaccaacaccagcatcctaggacttggtcttactctggcaag
```

The reverse primer was C1297synthr used in PCR(1). PCR (3) was performed at the same conditions as PCR(1).

The PCR(3) product had an approximate length of 700 bp and the PCR product was purified. The PCR products were suitable for a subsequent SOE PCR(4) fusion reaction. The signal peptide from the alkaline protease from *B. clausii* (aprH) was fused by SOE fusion as described in WO 99/43835 (hereby incorporated by reference) in frame to the DNA encoding the carbonic anhydrase that was obtained in PCR(3). The nucleotide fragments obtained from PCR(4) containing the carbonic anhydrase coding sequence were integrated by homologous recombination into the Bacillus subtilis host cell genome. The gene construct was expressed under the control of a triple promoter system (as described in WO 99/43835). The gene coding for chloramphenicol acetyltransferase was used as maker (as described in Diderichsen et al., 1993, *Plasmid* 30: 312-315).

Chloramphenicol resistant transformants were analyzed by DNA sequencing to verify the correct DNA sequence of the construct. The translated protein sequence corresponds to SEQ ID NO: 3, where amino acid 1-27 corresponds to the *B. clausii* aprH signal peptide, amino acids 28-34 corresponds to the HQ tag, amino acids 35-36 corresponds to the thrombin cleavage site and amino acids 37-260 corresponds to the predicted mature CA.

One expression clone was selected and was cultivated according to the procedure described in Example 1. Genomic DNA from the cultivated clone was prepared and used to transform a protease weak *B. subtilis* host strain. One expression clone from this protease weak strain was selected and was cultivated according to the procedure described in Example 1. It was determined that there was carbonic anhydrase activity in the culture broth according to Wilbur, 1948, *J. Biol. Chem.* 176: 147-154 (essentially as described in Example 5).

Example 3

Enzyme Purification

The culture broth from the protease weak *B. subtilis* host strain obtained in Example 2 was centrifuged (20000×g, 30 min) and the supernatants were clarified by filtration. Ammonium sulphate was added to 3.2 M final concentration and the precipitated protein was collected by centrifugation. The precipitated protein was dissolved in 5 volumes of deionised water and filtered through a NALGENE 0.2 micron Filtration unit (cat.no. 569-0020) to give a clear solution. The pH of the 0.2 micron filtrate was adjusted to pH 7.5 and the filtrate was applied to a Ni-sepharose FF column (GE Healthcare) equilibrated in 50 mM HEPES/NaOH, 500 mM NaCl, pH 7.5. After washing the Ni-sepharose FF column with the equilibration buffer, the column was washed extensively with the equilibration buffer with 10 mM Imidazole to remove loosely bound proteins. After these washes, the carbonic anhydrase was eluted by a step-elution with 50 mM HEPES/NaOH, 500 mM Imidazole, pH 7.5. The eluted peak was transferred to 10 mM MES/NaOH, pH 6.0 on a G25 sephadex column (GE Healthcare). The buffer changed solution was applied to a SOURCE 30S column (GE Healthcare) equilibrated in 10 mM MES/NaOH, pH 6.0. After washing the SOURCE 30S column extensively with the equilibration buffer, the enzyme was eluted with a linear NaCl gradient (0→0.5 M) in the same buffer over five column volumes. Fractions from the column were analyzed by SDS-PAGE and pure fractions were pooled. The pooled carbonic anhydrase solution was slightly coloured and therefore the solution was diluted 5× in deionized water and applied to a S-sepharose HP column (GE Healthcare) equilibrated in 10 mM MES/NaOH, pH 6.0. After washing the S-sepharose HP column extensively with the equilibration buffer, the enzyme was eluted by a step-elution with 10 mM MES/NaOH, 1 M NaCl, pH 6.0. Finally, the carbonic anhydrase peak was transferred to 50 mM HEPES/NaOH, 500 mM NaCl, pH 7.0 on a G25 sephadex column (GE Healthcare). Based on SDS Page the purity of the CA was estimated to be above 90%, the enzyme ran as a band with Mw=29 kDa. The buffer changed solution contained the purified CA preparation and was used for further characterization.

Example 4

Cloning, Expression and Purification of *Methanosarcina thermophila* TM-1 Carbonic Anhydrase A synthetic gene based on the protein sequence of the gamma-CA from *Methanosarcina thermophila* (UniProt: P40881) was designed and optimized for *B. subtilis*.

The synthetic gene was PCR amplified from the plasmid carrying the synthetic gene. A first PCR reaction (PCR(1)) was performed in a total volume of 50 microliters, the following reagents were added, 1 microliter of synthetic DNA preparation (template), 10 pmol of each of the primers (sgCAtspf and sgCAr), dNTPs and Phusion® polymerase (Finnzymes, Finland) in Phusion GC buffer. The PCR conditions were 94° C. for 2 min; 9 cycles of 94° C. for 15 sec; 55° C. for 45 sec; 68° C. for 1 min; followed by 68° C. for 10 min; 4° C. for 20 min and 15° C. until the end of the PCR program.

The primers used were:

```
sgCAtspf:
                                        (SEQ ID NO: 8)
cttgctgcctcattctgcagccgcgCAAGAGATCACTGTTGA sgCAr:
                                        (SEQ ID NO: 9)
tccgatccctttccattctactTTATGAAGTCTCTTTGTAGC
```

The PCR(1) product had an approximate length of 690 bp. The PCR product was purified and fused in frame by PCR(2) to the signal peptide from the alpha-amylase from *B. licheniformis* (AmyL). The nucleotide fragment obtained from PCR (2) containing the alpha-amylase signal peptide fused in frame to the gamma-carbonic anhydrase was integrated by homologous recombination on the *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as maker. (Described e.g., in Diderichsen et al., 1993, *Plasmid* 30: 312).

Chloramphenicol resistant transformants were analyzed by DNA sequencing to verify the correct DNA sequence of the construct. The translated protein sequence corresponds to SEQ ID NO: 7, where amino acid 1-28 corresponds to the AmyL signal peptide, amino acids 29-241 corresponds to the predicted mature gamma-CA.

One expression clone was selected and was cultivated in a 1 liter feed-batch fermentation for 34 days at 38° C. The pH was maintained at 6.8 with ammonium water during the fermentation. It was determined that there was carbonic anhydrase activity in the culture broth according to Wilbur, 1948, *J. Biol. Chem.* 176: 147-154 (essentially as described in Example 5).

The culture broth was centrifuged (26000×g, 20 min) and the supernatants were clarified by filtration. The filtrate was transferred to 10 mM HEPES/NaOH, pH 7.0 on a G25 sephadex column (GE Healthcare). The buffer exchanged enzyme solution was applied to a Q sepharose FF column (GE Healthcare) equilibrated in 20 mM HEPES/NaOH, pH 7.0. After washing the Q sepharose FF column extensively with the equilibration buffer, the enzyme was eluted with a linear NaCl gradient (0→0.5 M) in the same buffer over five column volumes. Fractions from the column were analyzed for CA activity and active fractions were pooled and diluted with deionized water to a conductivity of 4.2 mS/cm. The diluted CA pool was applied to a SOURCE 30Q column (GE Healthcare) equilibrated in 20 mM HEPES/NaOH, pH 7.0. After washing the SOURCE 30Q column extensively with the equilibration buffer, the enzyme was eluted with a linear NaCl gradient (0→0.5 M) in the same buffer over six column volumes. Fractions from the column were analyzed for CA activity and the most active fractions were pooled. Ammonium sulphate was added to the CA pool to a 2.0 M final concentration and the enzyme was applied to a Toyopearl Phenyl 650S column equilibrated in 10 mM HEPES/NaOH, 2.0 M $(NH_4)_2SO_4$, pH 7.0. After washing the Toyopearl Phenyl column extensively with the equilibration buffer, the enzyme was eluted with a linear $(NH_4)_2SO_4$ gradient (2.0→0 M) in the same buffer over six column volumes. Fractions from the column were analyzed for CA activity and the most active fractions were pooled as the purified product. The purified product was run on a 4-20% Tris-glycine Gold SDS-PAGE, which revealed a series of bands between 29 and 15 kDa, with the band at 29 kDa being the full-length mature CA. The bands were analyzed by N-terminal sequencing. All the sequences in the purified product matched CA from *M. thermophila*-however starting from different positions in the translated sequence. The bands between 23 kDa and 29 kDa are expected to contain active CA and constitute approximately 60% of the product.

Example 5

Detection of Carbonic Anhydrase Activity

The test for the detection of carbonic anhydrase was described by Wilbur, 1948, *J. Biol. Chem.* 176: 147-154. The set up is based on the pH change of the assay mixture due to the formation of bicarbonate from carbon dioxide as given in equation 1:

$$[CO2+H2O \rightarrow HCO3-+H+].$$

The activity assay used in this study was derived from the procedure of Chirica et al., 2001, *Biochim. Biophys. Acta* 1544(1-2): 55-63. A solution containing approximately 60 to 70 mM $CO_2$ was prepared by bubbling $CO_2$ into 100 ml distilled water using the tip of a syringe approximately 30 minutes prior to the assay. The $CO_2$ solution was chilled in a water-bath at 4° C. To test for the presence of carbonic anhydrase, 2 ml of 25 mM Tris adjusted to pH 8.3 with 25 mM HCl solution (containing sufficient bromothymol blue to give a distinct and visible blue color) were added to two 13×100 mm test tubes chilled in 4° C. water-bath. To one tube, 10 microliters of the enzyme containing solution (e.g., culture broth or purified enzyme) was added, and an equivalent amount of buffer was added to the second tube to serve as a control. 2 ml of $CO_2$ solution was added very quickly and smoothly to the bottom of each tube. Simultaneously with the addition of the $CO_2$ solution, a stopwatch was started. The time required for the solution to change from blue to yellow was recorded (transition point of bromothymol blue is pH 6-7.6). The production of hydrogen ions during the $CO_2$ hydration reaction lowers the pH of the solution until the color transition point of the bromothymol blue is reached. The time required for the color change is inversely related to the quantity of carbonic anhydrase present in the sample. The tubes must remain immersed in the ice bath for the duration of the assay for results to be reproducible. Typically, the uncatalyzed reaction (the control) takes 40 to 60 seconds for the color change to occur, whereas the enzyme catalyzed reaction is complete in 5 to 15 s, depending upon the amount of enzyme protein in the enzyme solution added. Detecting the color change is somewhat subjective but the error for triple measurements was in the range of 0 to 1 sec difference for the catalyzed reaction. One unit is defined after Wilbur [1 U=(1/tc)–(1/tu)×1000] where U is units and tc and tu represent the time in seconds for the catalyzed and uncatalyzed reaction, respectively (Wilbur, 1948, *J. Biol. Chem.* 176: 147-154). These units are also termed Wilbur-Anderson units (WAU).

Example 6

Heat-Stability of *Caminibacter* Carbonic Anhydrase

The melting temperature as well as activity of the carbonic anhydrase after treatment at increased temperature was assessed.

Differential Scanning Calorimetry (DSC)

The purified *Caminibacter* CA enzyme obtained in Example 3 was diluted to approx. 1 mg/ml in 50 mM HEPES/NaOH, pH 7.0 or 1 M Na-sesquicarbonate, pH 10.0. DSC was performed at a 90° C./hour scan rate from 20° C. to 120° C. in a VP DSC from MicroCal, MA. The melting point (temperature at top of denaturation peak in thermogramme) of the CA was 109° C. at pH 7.0 and 103° C. at pH 10. To the knowledge of the inventors this is the highest melting temperature of a carbonic anhydrase reported so far.

Temperature Stability Assay

The residual activity of the *Caminibacter* carbonic anhydrase of the present invention and the known thermophilic carbonic anhydrase from *M. thermophila* after heat treatment was assessed in relation to increasing temperature and increasing incubation time.

Stability as a Function of Increasing Temperature

The thermal stability of purified CA enzymes obtained from Examples 3 and 5 was measured as follows: 10 microliters of each enzyme was diluted 10 folds in 1 M $NaHCO_3$ at pH 8 and was incubated for 15 minutes at desired temperature. To measure tu, 1 M $NaHCO_3$ was heated at the same temperature this corresponds to the reaction time for uncatalyzed reaction as explained in Example 5. The samples were cooled down to room temperature and the carbonic anhydrase activity was measured using the Wilbur-Anderson assay described in Example 5.

The residual activity after incubation at elevated temperatures was calculated as the activity after heat-treatment divided by the activity of enzyme at 25° C. prior to the treatment times 100%. The results are presented in Table 1, which clearly shows that *Caminibacter* CA was superior in terms of thermostability over *M. thermophila* CA.

TABLE 1

Temperature stability after 15 min heat treatment in 1M $NaHCO_3$

| CA | Temperature [° C.] | | | | | | | | | | |
|---|---|---|---|---|---|---|---|---|---|---|---|
| | 25 | 37 | 50 | 55 | 60 | 65 | 70 | 75 | 80 | 90 | 100 |
| | Residual activity [%] | | | | | | | | | | |
| *Caminibacter* | 100 | n.d | 113 | n.d. | 126 | n.d. | 126 | n.d. | 132 | 101 | 40 |
| *M. thermophila* | 100 | 98 | 92 | n.d. | 79 | n.d. | 77 | n.d. | 17 | n.d | n.d | n.d. = not determined

Stability as a Function of Increasing Incubation Time

The two carbonic anhydrases obtained from Examples 3 and 5 were diluted 10 times with 1 M $NaHCO_3$ pH 8 or 0.1 M Britton-Robinson (B-R) buffer pH 8 (contains 62.4% by volume 0.1 M acids (0.1 M phosphoric acid, 0.1 M acetic acid, 0.1 M boric acid) and 37.6% by volume 0.5 M sodium hydroxide) and heated at 80° C. for the indicated time. The residual activity was measured as described above. The results are presented in Table 2, which clearly shows that *Caminibacter* carbonic anhydrase is capable of maintaining 83% residual activity in 1 M $NaHCO_3$ and 82% residual activity in 0.1 M Britton-Robinson buffer after incubation at 80° C. for 2 hours at pH 8.

TABLE 2

Residual activity after heat treatment at 80° C.

| Buffer | CA | Time [min] | | | | | |
|---|---|---|---|---|---|---|---|
| | | 0 | 15 | 30 | 40 | 60 | 120 |
| | | Residual activity [%] | | | | | |
| 1M $NaHCO_3$ | *Caminibacter* | 100 | 127 | 90 | n.d. | 91 | 83 |
| | *M. thermophila* | 100 | 19 | 0 | n.d. | n.d. | n.d. |

TABLE 2-continued

Residual activity after heat treatment at 80° C.

| Buffer | CA | Time [min] | | | | | |
|---|---|---|---|---|---|---|---|
| | | 0 | 15 | 30 | 40 | 60 | 120 |
| | | Residual activity [%] | | | | | |
| 0.1M B-R buffer | *Caminibacter* | 100 | 101 | n.d. | 102 | 89 | 82 |
| | *M. thermophila* | 100 | 23 | n.d. | 6 | n.d. | n.d. | n.d. = not determined

Example 7

Extraction of $CO_2$ from a Mixed Gas Stream in a Hollow Fiber Membrane Bioreactor A lab-scale hollow fiber membrane bioreactor (HFMB) was set up to selectively capture $CO_2$ from a gas stream which could resemble a flue gas.

Hollow Fiber Membrane Bioreactor Set-up

Porous hydrophobic hollow fiber membranes provide a high surface area of contact between the gas stream and carrier liquid. As a result they facilitate carbonation of a liquid or removal of $CO_2$ from a liquid. The selected module consists of 2300 parallel hollow fibers with $0.18\ m^2$ active surface area and average pore size of 0.01×0.04 micron ((Liqui-cel® MiniModule® 1×5.5 purchased from Membrana, N.C., USA). These membranes are easy to scale-up to industrial scale and have been used in industry for wastewater treatment and beverage carbonation. A schematic drawing of the bioreactor set-up is shown in FIG. 1. In the set-up carrier liquid was passed through the hollow fibers lumen using a positive displacement pump. The liquid flow rate was set to about 4 ml/min. The gas stream containing a mixture of 15% $CO_2$ (9 CCM) and 85% $N_2$ (51 CCM) (feed gas) entered the feed side of the hollow fibers counter-currently to the carrier liquid stream and the treated gas stream (scrubbed gas) exited the module at the sweep side of the hollow fibers. Two mass flow controllers were used to mix nitrogen and carbon dioxide with consistent concentration throughout the experiments. A mass flow meter was used to monitor the flow of the scrubbed gas as it exits the reactor. The gas and liquid flows and pressures were adjusted to avoid entering liquid to the gas phase and gas bubbles in the liquid phase of the module.

The purpose of this set-up was to demonstrate absorption of $CO_2$ into carrier liquid which results in hydration of $CO_2$ to bicarbonate. The absorption was measured by analyzing the $CO_2$ concentration in feed gas and scrubbed gas using a gas chromatograph (GC).

Carrier Liquid

A mixture of 1 M sodium bicarbonate and 1 M sodium hydroxide solution with pH=9 was used as a carrier liquid control. Then, 0.03 mg/mL of a carbonic anhydrase (CA) enzyme protein obtained from the purification described in Example 3, was added to the reservoir. The temperature was maintained at room temperature.

Gas Chromatography Method (GC-TCD)

A Shimadzu 2010 gas chromatograph with a thermal conductivity detector and a gas sampling valve was used for $CO_2$ concentration measurement. A capillary Carboxen Plot 1010 column was used to detect nitrogen and carbon dioxide. The column was heated isothermally for 7 minutes at 35° C., the temperature was increased with 20° C./min rate to 200° C. and it was maintained at 200° C. for 2 minutes. Injector and detector temperatures were maintained at 230° C. Column flow is 1 ml/min, split ratio 10 to 1 and carrier gas was helium. Nitrogen and carbon dioxide peaks were detected at retention times 6.4 and 15.3 minutes, respectively. The $CO_2$ peak was calibrated using three carbon dioxide standards with 0.1%, 1% and 10% by weight $CO_2$ in nitrogen purchased from Scott Specialty gases (Pennsylvania, USA).

Results

Table 3 shows the data collected from GC using carrier liquid with or without carbonic anhydrase. Each data point is the measurement from each injection during run time at room temperature. Data from the first injection from each set of measurements (carrier liquid with or without carbonic anhydrase) was disregarded to eliminate doubt about residual gas remained in the tubing or columns. The results indicate that 0.03 mg/mL carbonic anhydrase enzyme protein from *Caminibacter* increases the efficiency of $CO_2$ removal to about 80.0% compared to a control run at the same conditions without enzyme (~44.5%). Percent $CO_2$ in feed gas was averaged to be 17.4%.

TABLE 3

Effect of carrier liquid on the $CO_2$ concentration of the gas stream exiting the hollow fiber membrane bioreactor

| Carrier liquid | pH in reservoir | % CO2 in Scrubbed gas (avg) | % CO2 removed (avg) |
|---|---|---|---|
| 1M NaHCO₃ + NaOH | 9.0 | 9.6 ± 0.2 | 44.5 ± 1.2 |
| 1M NaHCO₃ + NaOH + 0.03 g/L CA | 9.0 | 3.5 ± 0.5 | 80.0 ± 2.6 |

Example 8

Extraction of $CO_2$ from a Mixed Gas Stream in a Hollow Fiber Membrane bioreactor after Heat Treatment of the Carbonic Anhydrase It was investigated whether the *Caminibacter* carbonic anhydrase of the present invention and another known thermostable carbonic anhydrase from *M. thermophila* were capable of extracting $CO_2$ after a pre-treatment at high temperature.

Heat Treatment

Solutions of *Caminibacter* CA obtained from Example 3 and *M. thermophila* CA obtained from Example 5 diluted 10 times with 1 M NaHCO₃ adjusted to pH=9±0.1 with 1 M NaOH were heated to 80° C. and maintained at 80° C. for 2 hours. After two hours, the solution was cooled down to room temperature and diluted with 1 M NaHCO₃/NaOH pH=9 solution to reach 0.03 mg/mL enzyme protein. These heat-treated enzyme solutions were used as carrier liquids in the hollow fiber membrane bioreactor set-up to compare the performance of the two enzymes versus a control solution, 1 M NaHCO₃/NaOH pH=9, in extraction of $CO_2$ from a mixed gas.

Analyzing $CO_2$ Extraction

A lab-scale hollow fiber membrane bioreactor (HFMB) assay to selectively capture $CO_2$ from a gas stream which could resemble a flue gas was set up, essentially as described in Example 7. The setup contained the following minor differences. The liquid flow rate was reduced to about 2 ml/min. Instead of adding the carbonic anhydrase to the carrier liquid after the control run the control carrier liquid was replaced with 150 mL of heat-treated solutions of CA containing 0.03 mg/mL enzyme protein as prepared above for each run. A new hollow fiber membrane module was used for each enzyme run to avoid contamination.

Results

Table 4 shows the data collected from GC using carrier liquid with or without carbonic anhydrase. Each data point is the measurement from each injection during run time at room temperature. Before each carbonic anhydrase, several injections of control carrier liquid were made and data from the first injection from each set of measurements (carrier liquid with or without carbonic anhydrase) was disregarded to eliminate doubt about residual gas remained in the tubing or columns. The results show that even after two hours of heat treatment at 80° C. in presence of high salt concentration, 0.03 mg/mL carbonic anhydrase enzyme protein from *Caminibacter* increases the efficiency of $CO_2$ removal to about 62% compared to a 44% $CO_2$ removal in a control run at the same conditions without enzyme. However, the known thermostable CA from *M. thermophila* at the same protein concentration did not change the $CO_2$ removal efficiency of the carrier solution (~38%) compared to control (~41%).

TABLE 4

Effect of carrier liquid on the $CO_2$ concentration of the gas stream exiting the hollow fiber membrane bioreactor

| | Carrier liquid | pH in reservoir | % CO2 in Scrubbed gas (Avg.) | % CO2 removed (Avg.) |
|---|---|---|---|---|
| Trial 1 *M. thermophila* CA | 1M (NaHCO₃ + NaOH) | 9.0 | 10.1 ± 0.03 | 40.9 ± 0.2 |
| | 1M (NaHCO₃ + NaOH) + 0.03 g/L CA | 9.0 | 10.5 ± 0.6 | 38.2 ± 3.3 |
| Trial 2 *Caminibacter* CA | 1M (NaHCO₃ + NaOH) | 9.0 | 10.3 ± 0.2 | 43.9 ± 0.8 |
| | 1M (NaHCO₃ + NaOH) + 0.03 g/L CA | 9.0 | 6.9 ± 0.1 | 62.4 ± 0.7 |

Example 9

Long Term Heat-Stability of *Caminibacter* Carbonic Anhydrase

The long-term thermal stability of *Caminibacter* CA enzyme obtained from Example 3 was measured at pH 8 as follows: 10 microliters of enzyme was diluted 10 folds in 0.1 M Britton-Robinson buffer at pH 8 and was incubated at 50° C. during the run time of experiment. To measure tu, 0.1 M Britton-Robinson buffer was heated at the same time at 50° C. this corresponds to the reaction time for uncatalyzed reaction as explained in Example 5. The samples were cooled to room temperature and the carbonic anhydrase activity was measured using the Wilbur-Anderson assay described in Example 5. The residual activity after incubation at different times is presented in Table 5. Results show that at pH 8, the *Caminibacter* CA enzyme retains more than 60% of its original activity after 30 days heating at 50° C.

TABLE 5

Residual activity during long-term heat treatment at 50° C. at pH 8 in 0.1M Britton-Robinson buffer

| CA | Residual activity (%) | | | | |
|---|---|---|---|---|---|
| | 15 min | 6 days | 14 day | 22 day | 30 day |
| *Caminibacter* | 100 | 80 | 64 | 65 | 63 |

Example 10

Identification of Carbonic Anhydrase (CA) Gene from *Caminibacter Hydrogeniphilus* DSM 14510

The partial genome of *Caminibacter hydrogeniphilus* DSM 14510 was sequenced using the commercially available Next-Generation DNA sequencing technology Illumina Solexa (Fasteris, Switzerland). The raw data of 10,242,572 sequences was assembled to 453 contigs, a technique that is known by the person skilled in the art. A part of the carbonic anhydrase gene was identified on contig number ZY504820 by BLASTP search using the *C. mediatlanticus* CA sequence of SEQ ID NO: 2 as search term. The full length enzyme was identified by manually assembly of several individual sequences and the coding sequence (SEQ ID NO: 12) was identified on contig denoted D6YWW. The translated protein sequence corresponds to SEQ ID NO: 13, where amino acid 1-22 corresponds to the signal peptide and amino acids 23-243 corresponds to the predicted mature CA. The CA encoding sequence, SEQ ID NO: 12, was verified by PCR amplification of a part of the genomic DNA covering the CA gene. One microliter of genomic DNA preparation (template), 10 pmol of each of the oligomers Chydrof and Chydror, dNTPs and Phusion® polymerase (Finnzymes, Finland) were mixed in Phusion GC buffer. The PCR conditions were as described in Example 1. The obtained PCR product (approx 800 bp, PCR conditions) was sequenced and confirmed by Sanger sequencing with the same oligomers and oliqo Chydroseq.

```
                                           (SEQ ID NO: 17)
Chydrof       ATACTTCTTTACAATTTTCTCG (SEQ ID NO: 18)
Chydror       AGAAGAGTGGAGTGATAAAAGG (SEQ ID NO: 19)
Chydroseq     TTTCTAAACAACGGCCATAC
```

Example 11

Cloning and Expression of Native *C. hydrogeniphilus* DSM 14510 CA Gene in *B. subtilis*

Essentially, the same procedure as described in Example 1 was used to clone the native CA gene into *B. subtilis*. Here, genomic DNA of *C. hydrogeniphilus* DSM 14510 was used as template and the oligomers C6224r and C6224f to amplify the gene by PCR.

```
                                           (SEQ ID NO: 20)
C6224r
CCA AGG CCG GTT TTT TAT GTT TTA TTT TAG TAT

TAC TCT TGC GTT (SEQ ID NO: 21)
C6224f
CAT CAG CAC CAA CAC CAG CAT ACA TGG AGC TAC

AGC GGA AAA AC
```

The fused gene fragment (SEQ ID NO: 14) was transformed into *B. subtilis* and expression of the enzyme (SEQ ID NO: 15) in one correct expression clone was done as described in Example 1. No CA activity was observed by the assay used in Example 5, indicating that the carbonic anhydrase gene of SEQ ID NO: 14 was not expressed in *B. subtilis*.

Example 12

Cloning and Expression of Synthetic *C. hydrogeniphilus* DSM 14510 CA Gene in *B. subtilis*

In order to enable the expression of CA from *C. hydrogeniphilus* DSM 14510, a synthetic gene coding for the carbonic anhydrase was designed. The synthetic gene was based on SEQ ID NO: 14. The codon usage was optimized for *B. subtilis* leading to the optimized sequence of SEQ ID NO: 16. The translation of SEQ ID NO: 16 corresponds to SEQ ID NO: 15, where amino acid 1-27 corresponds to the *B. clausii* aprH signal peptide, amino acids 28-34 is an affinity tag, amino acids 35-36 is a thrombin cleavage site and amino acids 37-257 corresponds to the predicted mature CA.

The cloning procedure and the expression of the synthetic gene followed the principles described in Example 11.

Weak CA expression was obtained from a correct CA expression clone as observed by SDS-PAGE analysis when compared to a *B. subtilis* expression host which lacks the carbonic anhydrase gene. One to three Wilbur units were measured in culture supernatants of the *B. subtilis* strain with the synthetic CA gene. The culture supernatant was treated for 15 min at 80° C. and no loss of CA activity was observed, indicating that the CA from *C. hydrogeniphilus* DSM 14510 is a heat stable enzyme.

Example 13

Immobilization of Carbonic Anhydrase on a Hollow Fiber Membrane Bioreactor

The ability of *Caminibacter* carbonic anhydrase of the present disclosure to absorb to a hollow fiber membrane made from polypropylene was measured by comparing the $CO_2$ scrubbing efficiency before and after washing the membrane, and further comparing to the $CO_2$ scrubbing performance of another carbonic anhydrase before and after washing the membrane. A lab-scale hollow fiber membrane bioreactor (HFMB) was set up as described in example 7 to selectively capture $CO_2$ from a gas stream which could resemble a flue gas.

Carrier Liquid

A mixture of 1 M sodium bicarbonate and 1 M sodium hydroxide solution with pH=9 was used as a carrier liquid control. Then, 0.03 mg/mL of a *Caminibacter* carbonic anhydrase enzyme protein obtained from the purification described in Example 3, or a *B. Clausii* carbonic anhydrase originating from *Bacillus clausii* KSM-K16 (Uniprot acc.

No. Q5WD44) was added to the reservoir. The temperature was maintained at room temperature. $CO_2$ scrubbing was carried out in the HFMB in the presence of the enzyme solutions as described in example 7 to measure "before washing" $CO_2$ scrubbing results. After the reservoir was emptied of enzyme solution, the reservoir was filled with washing solutions and washed as described below. $CO_2$ scrubbing was then carried out a second time using the washed HFMB to measure "after washing" $CO_2$ scrubbing results.

Membrane Washing $CO_2$ scrubbing efficiency of the membrane was measured before and after washing the membrane to illustrate that *Caminibacter* carbonic anhydrase can absorb to the membrane and deliver improved $CO_2$ scrubbing performance even after membrane washing compared to the no enzyme control. After the "before washing" $CO_2$ scrubbing results were collected, the membrane module was rinsed overnight with deionized water. Simulated flue gas was continuously passed through the module during this time. After rinsing with deionized water, the reservoir was filled with an aqueous solution of 1 M sodium bicarbonate adjusted to pH 9 with 1 M sodium hydroxide solution, which served as the carrier liquid for collecting the "after washing" $CO_2$ scrubbing results. No additional enzyme was added to this "after washing" carrier liquid. Therefore, improvement in $CO_2$ scrubbing efficiency can be attributed to enzyme that absorbed to the membrane prior to the washing step and remained available and active in the membrane after the washing step.

Results

Table 6 shows the data collected from GC using carrier liquid with or without carbonic anhydrase (CA), before and after washing the membrane. Each data point is the average of measurements from three injections during run time at room temperature. Percent $CO_2$ in feed gas was averaged to be 15%. Data from the first injection from each set of measurements (carrier liquid with or without carbonic anhydrase) was disregarded to eliminate doubt about residual gas remaining in the tubing or columns. The results show that "before washing" the presence of a solution of 0.03 mg/mL carbonic anhydrase enzyme protein from *Caminibacter* flowing at a rate of about 4 mL/min through the HFMB increases the efficiency of $CO_2$ removal to about 72.9% compared to a control run at the same conditions without enzyme (~27.9%). After washing the membrane, and without any additional enzyme added, data shows that $CO_2$ removal of 73.4% was achieved. This result demonstrates that *Caminibacter* carbonic anhydrase was absorbed or immobilized on the polypropylene membrane during the "before washing" step and was not washed off by deionized water or by fresh bicarbonate carrier liquid. The same "before/after" procedure was followed using a 0.03 mg/mL solution of carbonic anhydrase from *B. Clausii* in the hollow fiber membrane bioreactor. Table 6 shows that "before washing" the membrane addition of carbonic anhydrase from *B. Clausii* increases the efficiency of $CO_2$ removal to about 75.2% compared to a control run at the same conditions without enzyme (~29.7%). However, after washing the membrane the $CO_2$ removal efficiency was reduced to 23.8%, which is similar to the $CO_2$ scrubbing efficiency of the control treatment where enzyme is never present. This data shows that *Caminibacter* carbonic anhydrase can effectively absorb onto and adhere to polypropylene surfaces compared to other carbonic anhydrases. This ability to absorb to surfaces is a beneficial property for techniques and processes involving enzyme immobilization.

Table 6 Effect of carrier liquid on the $CO_2$ concentration of the gas stream exiting the hollow fiber membrane bioreactor before and after washing step

TABLE 6

| Carrier liquid | % $CO_2$ in Scrubbed gas (avg) | % $CO_2$ removed (avg) |
|---|---|---|
| 1M $NaHCO_3$ + NaOH | 10.5 ± 0.1 | 27.9 ± 0.5 |
| 1M $NaHCO_3$ + NaOH + 0.03 g/L *Caminibacter* CA before washing | 3.9 ± 0.1 | 72.9 ± 0.8 |
| 1M $NaHCO_3$ + NaOH after washing | 4.1 ± 0.1 | 73.4 ± 0.4 |
| 1M $NaHCO_3$ + NaOH | 10.1 ± 0.1 | 29.7 ± 1.0 |
| 1M $NaHCO_3$ + NaOH + 0.03 g/L *B. Clausii* CA before washing | 3.6 ± 0.0 | 75.2 ± 0.2 |
| 1M $NaHCO_3$ + NaOH after washing | 11.0 ± 0.1 | 23.8 ± 0.9 |

Example 14

Immobilization of Carbonic Anhydrase in a Column Packed with Nylon Pellets

A lab-scale packed column bioreactor was set up to selectively capture $CO_2$ from a gas stream which could resemble a flue gas. The reactor was constructed using a jacketed glass column where the flue gas enters the column from bottom and the absorption solution drips from column top. The absorption takes place on the column packing which can be pellets or beads that can be immobilized with carbonic anhydrase. The column's performance was tested with an aqueous solution of 1 M sodium bicarbonate adjusted to pH 9 with 1 M sodium hydroxide solution as carrier liquid with and without CA in solution and microporous nylon particles as packing material. Nylon pellets (Accurel microporous polymer—Polyamide 6 pellets XP700) provided by Membrana GmbH, 42289 Wuppertal, Germany were soaked in an aqueous solution of 1 M sodium bicarbonate adjusted to pH 9 with 1 M sodium hydroxide solution for 35 min. The particles were then packed into the packed column reactor. The carrier liquid was then dripped into the top of the column while a simulated flue gas stream containing 15% $CO_2$ was bubbled in the bottom of the column. Scrubbed gas from the top of the column was sent to a GC using method described in Example 7. After collecting all the data needed for control, carbonic anhydrase from *Caminibacter* of the present disclosure was added to the carrier liquid and scrubbed gas data was collected. Table 7 shows the data collected from GC using carrier liquid with or without carbonic anhydrase (CA). Each data point is the average of measurements from three injections during run time at room temperature. Data from the first injection from each set of measurements (carrier liquid with or without carbonic anhydrase) was disregarded to eliminate doubt about residual gas remaining in the tubing or columns. The results indicated that in this example 0.03 mg/mL carbonic anhydrase enzyme protein from *Caminibacter* increased the efficiency of $CO_2$ removal to about 58% compared to a control run at the same conditions without enzyme (~16.4%). The enzyme solution was circulated through the column overnight to assure that the maximum amount of enzyme was adsorbed onto the column. The next day the column was rinsed with deionized water for one hour. The deionized water was then replaced with an aqueous solution of 1 M sodium bicarbonate adjusted to pH 9 with 1 M sodium hydroxide solution and the $CO_2$ content of the scrubbed gas was measured after this washing step for carrier liquid without any additional enzyme added. Data showed that even after washing step overnight a $CO_2$ removal of 32.0% can be achieved.

Therefore the CA enzyme has been immobilized on the pellets. The same procedure was followed using carbonic anhydrase from *B. Clausii* in the packed column bioreactor. Table 7 shows that addition of carbonic anhydrase from *B. Clausii* increases the efficiency of $CO_2$ removal to about 52.9% compared to a control run at the same conditions without enzyme (~16.6%). However, when the module was rinsed with deionized water followed by an aqueous solution of 1 M sodium bicarbonate adjusted to pH 9 with 1 M sodium hydroxide solution, the enzyme washed off the membrane module easily and the $CO_2$ removal efficiency was reduced back to 21.6%. The data showed that immobilization could be achieved by this procedure only using the *Caminibacter* carbonic anhydrase which makes it a particularly suitable enzyme for immobilization.

Table 7 Effect of carrier liquid on the $CO_2$ concentration of the gas stream exiting the packed column bioreactor before and after washing step

TABLE 7

| Carrier liquid | % $CO_2$ in Scrubbed gas (avg) | % $CO_2$ removed (avg) |
|---|---|---|
| 1M NaHCO$_3$ + NaOH | 12.5 ± 0.6 | 16.4 ± 3.9 |
| 1M NaHCO$_3$ + NaOH + 0.03 | 6.3 ± 1.1 | 58.0 ± 7.4 |

TABLE 7-continued

| Carrier liquid | % $CO_2$ in Scrubbed gas (avg) | % $CO_2$ removed (avg) |
|---|---|---|
| g/L *Caminibacter* CA before washing | | |
| 1M NaHCO$_3$ + NaOH after washing | 10.2 ± 0.4 | 32.0 ± 2.4 |
| 1M NaHCO$_3$ + NaOH | 12.6 ± 0.1 | 16.6 ± 0.7 |
| 1M NaHCO$_3$ + NaOH + 0.03 g/L *B. Clausii* CA before washing | 7.1 ± 0.5 | 52.9 ± 3.1 |
| 1M NaHCO$_3$ + NaOH after washing | 11.8 ± 0.6 | 21.6 ± 3.9 |

It will be understood that various modifications may be made to the embodiments disclosed herein. Therefore, the above description should not be construed as limiting, but merely as exemplifications of embodiments. Those skilled in art will envision other modifications within the scope and spirit of the claims appended hereto.

The invention claimed is:

1. A process for extracting carbon dioxide comprising treating a carbon dioxide-containing medium with a carbonic anhydrase, wherein the carbonic anhydrase is a polypeptide which is at least 80% identical to amino acid residues 28 to 259 or 36 to 259 of SEQ ID NO: 2, or at least 80% identical to amino acid residues 23 to 243 of SEQ ID NO: 13.

2. The process of claim 1, wherein the carbonic anhydrase is a *Caminibacter* carbonic anhydrase.

3. The process of claim 1, wherein the *Caminibacter* carbonic anhydrase is a *Caminibacter hydrogeniphilus, Caminibacter mediatlanticus* or *Caminibacter profundus* carbonic anhydrase.

4. The process of claim 1, wherein the *Caminibacter* carbonic anhydrase is obtainable from or producible by *Caminibacter hydrogeniphilus* DSM 14510, *Caminibacter mediatlanticus* DSM 16658 or *Caminibacter profundus* DSM 15016.

5. The process of claim 1, wherein the carbonic anhydrase is a polypeptide which is at least 90% identical to amino acid residues 28 to 259 or 36 to 259 of SEQ ID NO: 2.

6. The process of claim 1, wherein the carbonic anhydrase is a polypeptide which is at least 95% identical to amino acid residues 28 to 259 or 36 to 259 of SEQ ID NO: 2.

7. The process of claim 1, wherein the carbonic anhydrase is a polypeptide which is at least 97% identical to amino acid residues 28 to 259 or 36 to 259 of SEQ ID NO: 2.

8. The process of claim 1, wherein the carbonic anhydrase is a polypeptide which is at least 98% identical to amino acid residues 28 to 259 or 36 to 259 of SEQ ID NO: 2.

9. The process of claim 1, wherein the carbonic anhydrase is a polypeptide which is at least 99% identical to amino acid residues 28 to 259 or 36 to 259 of SEQ ID NO: 2.

10. The process of claim 1, wherein the carbonic anhydrase is a polypeptide which comprises amino acid residues 28 to 259 or 36 to 259 of SEQ ID NO: 2.

11. The process of claim 1, wherein the carbonic anhydrase is a polypeptide which is at least 90% identical to amino acid residues 23 to 243 of SEQ ID NO: 13.

12. The process of claim 1, wherein the carbonic anhydrase is a polypeptide which is at least 95% identical to amino acid residues 23 to 243 of SEQ ID NO: 13.

13. The process of claim 1, wherein the carbonic anhydrase is a polypeptide which is at least 97% identical to amino acid residues 23 to 243 of SEQ ID NO: 13.

14. The process of claim 1, wherein the carbonic anhydrase is a polypeptide which is at least 98% identical to amino acid residues 23 to 243 of SEQ ID NO: 13.

15. The process of claim 1, wherein the carbonic anhydrase is a polypeptide which is at least 99% identical to amino acid residues 23 to 243 of SEQ ID NO: 13.

16. The process of claim 1, wherein the carbonic anhydrase is a polypeptide which comprises amino acid residues 23 to 243 of SEQ ID NO: 13.

17. The process of claim 1, wherein the carbonic anhydrase maintains at least 30% residual activity after 15 minutes at a temperature of 55° C.

18. The process of claim 1, wherein the carbon dioxide-containing medium is a gas or a multiphase mixture selected from the group consisting of a flue gas, a raw natural gas, a syngas, and a biogas.

19. The process of claim 1, wherein the carbon dioxide-containing medium is a bicarbonate-containing liquid and the carbon dioxide extraction is the conversion of bicarbonate to carbon dioxide.

20. The process of claim 1, wherein the extraction of carbon dioxide is performed at temperatures between 55° C. and 120° C.

* * * * *

SEQUENCE LISTING

```
<160> NUMBER OF SEQ ID NOS: 22

<210> SEQ ID NO 1
<211> LENGTH: 675
<212> TYPE: DNA
<213> ORGANISM: Caminibacter mediatlanticus

<400> SEQUENCE: 1
acttggagtt atagtggaaa aactggacct gagtattggg gagatttaaa aaaagaatat    60
caaatgtgta aaattgggaa aaatcaatca ccaattgata tcaaaacaaa ttcaactcaa    120
acatttaata caaacttaaa accatttaaa attaaatatt taggtaaagg ttatgaagta    180
ataaacaatg gtcatacaat taaagtaaaa acagaaggca aaaactgtgt tagaattgat    240
ggtattaaat ttaaattagc acaacttcac tttcatacac caagtgaaaa tacaataaat    300
ggaaaacatt ttccaatgga agcacactat gtacatttag ataaaaatgg aaacattaca    360
gttttagcgg ttatgtataa aataggtaaa gaaataaat cattaaataa aatgttagct    420
gttttaccaa caaaagttgg tgaagaaaat aaagttatgg gtaatctaaa tccaatggaa    480
ttattaccaa aaaataaagc atattataga tttaatggtt cattaacaac tccaccttgt    540
agtgaaggtg ttagatggat agtatttaaa acaccagttg agatttcaca agctcaatat    600
gaaaaaatgc acgctgtaat gggtactaac aatagaccag tccagccaat taatgcaagg    660
gttattttaa aataa                                                    675

<210> SEQ ID NO 2
<211> LENGTH: 259
<212> TYPE: PRT
<213> ORGANISM: Artificial Sequence
<220> FEATURE:
<223> OTHER INFORMATION: Fusion of Savinase signal peptide and CA from
      C.mediatlanicus

<400> SEQUENCE: 2

Met Lys Lys Pro Leu Gly Lys Ile Val Ala Ser Thr Ala Leu Leu Ile
1               5                   10                  15
```

```
Ser Val Ala Phe Ser Ser Ser Ile Ala Ser Ala Ser Ser Tyr Asn
                20                  25                  30

Tyr His Ala Thr Trp Ser Tyr Ser Gly Lys Thr Gly Pro Glu Tyr Trp
             35                  40                  45

Gly Asp Leu Lys Lys Glu Tyr Gln Met Cys Lys Ile Gly Lys Asn Gln
 50                  55                  60

Ser Pro Ile Asp Ile Lys Thr Asn Ser Thr Gln Thr Phe Asn Thr Asn
 65                  70                  75                  80

Leu Lys Pro Phe Lys Ile Lys Tyr Leu Gly Lys Gly Tyr Glu Val Ile
                 85                  90                  95

Asn Asn Gly His Thr Ile Lys Val Lys Thr Glu Gly Lys Asn Cys Val
                100                 105                 110

Arg Ile Asp Gly Ile Lys Phe Lys Leu Ala Gln Leu His Phe His Thr
                115                 120                 125

Pro Ser Glu Asn Thr Ile Asn Gly Lys His Phe Pro Met Glu Ala His
130                 135                 140

Tyr Val His Leu Asp Lys Asn Gly Asn Ile Thr Val Leu Ala Val Met
145                 150                 155                 160

Tyr Lys Ile Gly Lys Glu Asn Lys Ser Leu Asn Lys Met Leu Ala Val
                165                 170                 175

Leu Pro Thr Lys Val Gly Glu Glu Asn Lys Val Met Gly Asn Leu Asn
                180                 185                 190

Pro Met Glu Leu Leu Pro Lys Asn Lys Ala Tyr Tyr Arg Phe Asn Gly
                195                 200                 205

Ser Leu Thr Thr Pro Pro Cys Ser Glu Gly Val Arg Trp Ile Val Phe
                210                 215                 220

Lys Thr Pro Val Glu Ile Ser Gln Ala Gln Tyr Glu Lys Met His Ala
225                 230                 235                 240

Val Met Gly Thr Asn Asn Arg Pro Val Gln Pro Ile Asn Ala Arg Val
                245                 250                 255

Ile Leu Lys

<210> SEQ ID NO 3
<211> LENGTH: 260
<212> TYPE: PRT
<213> ORGANISM: Artificial Sequence
<220> FEATURE:
<223> OTHER INFORMATION: Polypeptide with savinase signal peptide, HQ
      tag, Throbin cleavage site and CA from C.mediatlanicus

<400> SEQUENCE: 3

Met Lys Lys Pro Leu Gly Lys Ile Val Ala Ser Thr Ala Leu Leu Ile
 1               5                  10                  15

Ser Val Ala Phe Ser Ser Ser Ile Ala Ser Ala His Gln His Gln His
                20                  25                  30

Gln His Pro Arg Thr Trp Ser Tyr Ser Gly Lys Thr Gly Pro Glu Tyr
             35                  40                  45

Trp Gly Asp Leu Lys Lys Glu Tyr Gln Met Cys Lys Ile Gly Lys Asn
 50                  55                  60

Gln Ser Pro Ile Asp Ile Lys Thr Asn Ser Thr Gln Thr Phe Asn Thr
 65                  70                  75                  80

Asn Leu Lys Pro Phe Lys Ile Lys Tyr Leu Gly Lys Gly Tyr Glu Val
                 85                  90                  95

Ile Asn Asn Gly His Thr Ile Lys Val Lys Thr Glu Gly Lys Asn Cys
                100                 105                 110
```

```
Val Arg Ile Asp Gly Ile Lys Phe Lys Leu Ala Gln Leu His Phe His
        115                 120                 125

Thr Pro Ser Glu Asn Thr Ile Asn Gly Lys His Phe Pro Met Glu Ala
        130                 135                 140

His Tyr Val His Leu Asp Lys Asn Gly Asn Ile Thr Val Leu Ala Val
145                 150                 155                 160

Met Tyr Lys Ile Gly Lys Glu Asn Lys Ser Leu Asn Lys Met Leu Ala
                165                 170                 175

Val Leu Pro Thr Lys Val Gly Glu Glu Asn Lys Val Met Gly Asn Leu
            180                 185                 190

Asn Pro Met Glu Leu Leu Pro Lys Asn Lys Ala Tyr Tyr Arg Phe Asn
        195                 200                 205

Gly Ser Leu Thr Thr Pro Pro Cys Ser Glu Gly Val Arg Trp Ile Val
    210                 215                 220

Phe Lys Thr Pro Val Glu Ile Ser Gln Ala Gln Tyr Glu Lys Met His
225                 230                 235                 240

Ala Val Met Gly Thr Asn Asn Arg Pro Val Gln Pro Ile Asn Ala Arg
                245                 250                 255

Val Ile Leu Lys
        260

<210> SEQ ID NO 4
<211> LENGTH: 47
<212> TYPE: DNA
<213> ORGANISM: Artificial Sequence
<220> FEATURE:
<223> OTHER INFORMATION: Primer

<400> SEQUENCE: 4
tttagttcat cgatcgcatc ggctgcgtct tcttacaact accacgc          47

<210> SEQ ID NO 5
<211> LENGTH: 47
<212> TYPE: DNA
<213> ORGANISM: Artificial Sequence
<220> FEATURE:
<223> OTHER INFORMATION: primer

<400> SEQUENCE: 5
gccaaggccg gttttttatg ttttacttaa ggattacgcg agcattg          47

<210> SEQ ID NO 6
<211> LENGTH: 48
<212> TYPE: DNA
<213> ORGANISM: Artificial Sequence
<220> FEATURE:
<223> OTHER INFORMATION: primer

<400> SEQUENCE: 6
catcagcacc aacaccagca tcctaggact tggtcttact ctggcaag         48

<210> SEQ ID NO 7
<211> LENGTH: 241
<212> TYPE: PRT
<213> ORGANISM: Artificial Sequence
<220> FEATURE:
<223> OTHER INFORMATION: alpha-amylase signal peptide fused to
      Methanosarcina thermophila TM-1 carbonic anhydrase

<400> SEQUENCE: 7

Met Lys Gln Gln Lys Arg Leu Tyr Ala Arg Leu Leu Thr Leu Leu Phe
```

```
  1               5                  10                 15
Ala Leu Ile Phe Leu Pro His Ser Ala Ala Gln Glu Ile Thr
             20                 25                 30

Val Asp Glu Phe Ser Asn Ile Arg Glu Asn Pro Val Thr Pro Trp Asn
             35                 40                 45

Pro Glu Pro Ser Ala Pro Val Ile Asp Pro Thr Ala Tyr Ile Asp Pro
         50                 55                 60

Gln Ala Ser Val Ile Gly Glu Val Thr Ile Gly Ala Asn Val Met Val
 65                 70                 75                 80

Ser Pro Met Ala Ser Ile Arg Ser Asp Glu Gly Met Pro Ile Phe Val
                 85                 90                 95

Gly Asp Arg Ser Asn Val Gln Asp Gly Val Val Leu His Ala Leu Glu
                100                105                110

Thr Ile Asn Glu Glu Gly Glu Pro Ile Glu Asp Asn Ile Val Glu Val
                115                120                125

Asp Gly Lys Glu Tyr Ala Val Tyr Ile Gly Asn Asn Val Ser Leu Ala
            130                135                140

His Gln Ser Gln Val His Gly Pro Ala Ala Val Gly Asp Asp Thr Phe
145                150                155                160

Ile Gly Met Gln Ala Phe Val Phe Lys Ser Lys Val Gly Asn Asn Cys
                165                170                175

Val Leu Glu Pro Arg Ser Ala Ala Ile Gly Val Thr Ile Pro Asp Gly
                180                185                190

Arg Tyr Ile Pro Ala Gly Met Val Val Thr Ser Gln Ala Glu Ala Asp
            195                200                205

Lys Leu Pro Glu Val Thr Asp Asp Tyr Ala Tyr Ser His Thr Asn Glu
            210                215                220

Ala Val Val Tyr Val Asn Val His Leu Ala Glu Gly Tyr Lys Glu Thr
225                230                235                240

Ser

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
cttgctgcct cattctgcag ccgcgcaaga gatcactgtt ga                          42

<210> SEQ ID NO 9
<211> LENGTH: 44
<212> TYPE: DNA
<213> ORGANISM: Artificial Sequence
<220> FEATURE:
<223> OTHER INFORMATION: primer

<400> SEQUENCE: 9
tccgatcccc ttttccattc tactttatga agtctctttg tagc                        44

<210> SEQ ID NO 10
<211> LENGTH: 12
<212> TYPE: PRT
<213> ORGANISM: Artificial Sequence
<220> FEATURE:
<223> OTHER INFORMATION: alignment example

<400> SEQUENCE: 10
```

Ala Cys Met Ser His Thr Trp Gly Glu Arg Asn Leu
1               5                   10

<210> SEQ ID NO 11
<211> LENGTH: 14
<212> TYPE: PRT
<213> ORGANISM: Artificial Sequence
<220> FEATURE:
<223> OTHER INFORMATION: alignment example

<400> SEQUENCE: 11

His Gly Trp Gly Glu Asp Ala Asn Leu Ala Met Asn Pro Ser
1               5                   10

<210> SEQ ID NO 12
<211> LENGTH: 732
<212> TYPE: DNA
<213> ORGANISM: Caminibacter hydrogeniphilus

<400> SEQUENCE: 12

```
atgaaaaaaa tattaacaat cgcggcactt gcttcagcaa tgttcgcaag caactacgca      60
catggcacat ggagctacag cggaaaaaca ggtcctgaat actggggaga cttaaaaccg     120
gaatataaaa tgtgtaaaat aggaaaaaat caatctccta ttgatatcag tggagctgta     180
agcgctactc ttacacctgt aaatatttac tatgacgtaa aagcaaaaac atttctaaac     240
aacggccata ctttaaaagc tgaaatgaaa gacggagcaa aactctatat agacggaaaa     300
gaatttagac tgcttcagtt ccatttccat accccaagcg aaaacacaat aaacggtgaa     360
tattttccaa tggaaggaca ttttgttcat tctacaaaag acggtgagct agcggtagta     420
tctgtaatgt ttaaaatcgg taaatataat cccgctattc aaaaacttat aaataatatg     480
ccaaaacacg cgggtgagaa gaaaaatatc tgttctgcta atctaaaagc aaaagattta     540
ttgccaaaaa gtttagagta ttacagattt aacggttctt taaccactcc tccttgtact     600
gaaggggtta gatggttcgt attaaaagaa cctgttcaaa tgagcgccaa gcaggtaaaa     660
gaatttgaaa aaattatggg taaaaacaac cgcccaatcc aaccaatcaa cgcaagagta     720
atactaaaat aa                                                         732
```

<210> SEQ ID NO 13
<211> LENGTH: 243
<212> TYPE: PRT
<213> ORGANISM: Caminibacter hydrogeniphilus

<400> SEQUENCE: 13

Met Lys Lys Ile Leu Thr Ile Ala Ala Leu Ala Ser Ala Met Phe Ala
1               5                   10                  15

Ser Asn Tyr Ala His Gly Thr Trp Ser Tyr Ser Gly Lys Thr Gly Pro
            20                  25                  30

Glu Tyr Trp Gly Asp Leu Lys Pro Glu Tyr Lys Met Cys Lys Ile Gly
        35                  40                  45

Lys Asn Gln Ser Pro Ile Asp Ile Ser Gly Ala Val Ser Ala Thr Leu
    50                  55                  60

Thr Pro Val Asn Ile Tyr Tyr Asp Val Lys Ala Lys Thr Phe Leu Asn
65                  70                  75                  80

Asn Gly His Thr Leu Lys Ala Glu Met Lys Asp Gly Ala Lys Leu Tyr
                85                  90                  95

Ile Asp Gly Lys Glu Phe Arg Leu Leu Gln Phe His Phe His Thr Pro
            100                 105                 110

```
Ser Glu Asn Thr Ile Asn Gly Glu Tyr Phe Pro Met Glu Gly His Phe
        115                 120                 125

Val His Ser Thr Lys Asp Gly Glu Leu Ala Val Ser Val Met Phe
    130                 135                 140

Lys Ile Gly Lys Tyr Asn Pro Ala Ile Gln Lys Leu Ile Asn Asn Met
145                 150                 155                 160

Pro Lys His Ala Gly Glu Lys Lys Asn Ile Cys Ser Ala Asn Leu Lys
                165                 170                 175

Ala Lys Asp Leu Leu Pro Lys Ser Leu Glu Tyr Tyr Arg Phe Asn Gly
            180                 185                 190

Ser Leu Thr Thr Pro Pro Cys Thr Glu Gly Val Arg Trp Phe Val Leu
        195                 200                 205

Lys Glu Pro Val Gln Met Ser Ala Lys Gln Val Lys Glu Phe Glu Lys
    210                 215                 220

Ile Met Gly Lys Asn Asn Arg Pro Ile Gln Pro Ile Asn Ala Arg Val
225                 230                 235                 240

Ile Leu Lys

<210> SEQ ID NO 14
<211> LENGTH: 774
<212> TYPE: DNA
<213> ORGANISM: Artificial Sequence
<220> FEATURE:
<223> OTHER INFORMATION: Fusion of Savinase signal peptide and CA from
      C.hydrogeniphilus

<400> SEQUENCE: 14
atgaagaaac cgttggggaa aattgtcgca agcaccgcac tactcatttc tgttgctttt      60
agttcatcga tcgcatcggc tcatcagcac caacaccagc atcctaggac atggagctac    120
agcggaaaaa caggtcctga atactgggga gacttaaaac cggaatataa aatgtgtaaa    180
ataggaaaaa atcaatctcc tattgatatc agtggagctg taagcgctac tcttacacct    240
gtaaatattt actatgacgt aaaagcaaaa acatttctaa caacggcca tactttaaaa     300 gctgaaatga agacggagc aaaactctat atagacggaa agaatttag actgcttcag     360 ttccatttcc ataccccaag cgaaaacaca ataaacggtg aatattttcc aatggaagga    420
cattttgttc attctacaaa agacggtgag ctagcggtag tatctgtaat gtttaaaatc    480
ggtaaatata atcccgctat tcaaaaactt ataataata tgccaaaaca cgcgggtgag    540
aagaaaaata tctgttctgc taatctaaaa gcaaagatt tattgccaaa agtttagag     600 tattacagat ttaacggttc tttaaccact cctccttgta ctgaagggt tagatggttc    660 gtattaaaag aacctgttca atgagcgcc aagcaggtaa aagaatttga aaaaattatg    720
ggtaaaaaca accgcccaat ccaaccaatc aacgcaagag taatactaaa ataa         774

<210> SEQ ID NO 15
<211> LENGTH: 257
<212> TYPE: PRT
<213> ORGANISM: Artificial Sequence
<220> FEATURE:
<223> OTHER INFORMATION: Fusion of Savinase signal peptide and CA from
      C.hydrogeniphilus

<400> SEQUENCE: 15

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala His Gln His Gln His
```

```
                20                  25                  30
Gln His Pro Arg Thr Trp Ser Tyr Ser Gly Lys Thr Gly Pro Glu Tyr
             35                  40                  45

Trp Gly Asp Leu Lys Pro Glu Tyr Lys Met Cys Lys Ile Gly Lys Asn
 50                  55                  60

Gln Ser Pro Ile Asp Ile Ser Gly Ala Val Ser Ala Thr Leu Thr Pro
 65                  70                  75                  80

Val Asn Ile Tyr Tyr Asp Val Lys Ala Lys Thr Phe Leu Asn Asn Gly
                 85                  90                  95

His Thr Leu Lys Ala Glu Met Lys Asp Gly Ala Lys Leu Tyr Ile Asp
             100                 105                 110

Gly Lys Glu Phe Arg Leu Leu Gln Phe His Phe His Thr Pro Ser Glu
             115                 120                 125

Asn Thr Ile Asn Gly Glu Tyr Phe Pro Met Glu Gly His Phe Val His
 130                 135                 140

Ser Thr Lys Asp Gly Glu Leu Ala Val Val Ser Val Met Phe Lys Ile
145                 150                 155                 160

Gly Lys Tyr Asn Pro Ala Ile Gln Lys Leu Ile Asn Asn Met Pro Lys
                165                 170                 175

His Ala Gly Glu Lys Lys Asn Ile Cys Ser Ala Asn Leu Lys Ala Lys
             180                 185                 190

Asp Leu Leu Pro Lys Ser Leu Glu Tyr Tyr Arg Phe Asn Gly Ser Leu
             195                 200                 205

Thr Thr Pro Pro Cys Thr Glu Gly Val Arg Trp Phe Val Leu Lys Glu
 210                 215                 220

Pro Val Gln Met Ser Ala Lys Gln Val Lys Glu Phe Glu Lys Ile Met
225                 230                 235                 240

Gly Lys Asn Asn Arg Pro Ile Gln Pro Ile Asn Ala Arg Val Ile Leu
                245                 250                 255

Lys

<210> SEQ ID NO 16
<211> LENGTH: 774
<212> TYPE: DNA
<213> ORGANISM: Artificial Sequence
<220> FEATURE:
<223> OTHER INFORMATION: codon optimized C.hydrogeniphilus gene

<400> SEQUENCE: 16
atgaagaaac cgttggggaa aattgtcgca agcaccgcac tactcatttc tgttgctttt      60
agttcatcga tcgcatcggc tcatcagcac caacaccagc atcctaggac atggtcttac     120
tcaggcaaga caggtccgga gtactggggt gaccttaagc ctgagtacaa gatgtgtaag     180
atcggcaaga accagtctcc aatcgacatc tcaggtgcgg tttcagcgac acttacacca     240
gttaacatct actacgacgt aaaggctaag actttcctta caacggcca cacacttaag      300 gctgagatga aggatggcgc aaagctttac atcgacggca aggagttccg ccttcttcaa     360
ttccatttcc acacaccttc tgagaacact atcaacggcg agtacttccc tatggagggc     420
cacttcgttc actctacaaa ggacggcgag cttgcggtag tttctgttat gttcaagatc     480
ggcaagtaca acccagctat ccaaaagctt atcaacaaca tgcctaagca cgctggcgag     540
aagaagaaca tctgttcagc gaaccttaag gcaaaggacc ttcttccgaa gtcacttgag     600
tactaccgct tcaacggctc acttacaact ccaccatgta cagagggcgt tcgctggttc     660
gttcttaagg agccagtaca aatgtcagcg aagcaagtta aggagttcga agatcatg       720
```

```
ggcaagaaca atcgcccaat ccaaccaatc aatgctcgcg ttatccttaa gtaa         774
```

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17

```
atacttcttt acaatttct cg                                              22
```

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18

```
agaagagtgg agtgataaaa gg                                             22
```

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19

```
tttctaaaca acggccatac                                                20
```

<210> SEQ ID NO 20
<211> LENGTH: 45
<212> TYPE: DNA
<213> ORGANISM: Artificial Sequence
<220> FEATURE:
<223> OTHER INFORMATION: primer

<400> SEQUENCE: 20

```
ccaaggccgg tttttatgt tttattttag tattactctt gcgtt                    45
```

<210> SEQ ID NO 21
<211> LENGTH: 44
<212> TYPE: DNA
<213> ORGANISM: Artificial Sequence
<220> FEATURE:
<223> OTHER INFORMATION: primer

<400> SEQUENCE: 21

```
catcagcacc aacaccagca tacatggagc tacagcggaa aaac                    44
```

<210> SEQ ID NO 22
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa at position 3 is H or N
<220> FEATURE:
<221> NAME/KEY: misc_feature
<222> LOCATION: (4)..(4)
<223> OTHER INFORMATION: Xaa at position 4 is any amino acid
<220> FEATURE:

```
<221> NAME/KEY: misc_feature
<222> LOCATION: (5)..(5)
<223> OTHER INFORMATION: Xaa at position 5 is L, I, V or M
<220> FEATURE:
<221> NAME/KEY: misc_feature
<222> LOCATION: (6)..(9)
<223> OTHER INFORMATION: Xaa at positions 6, 7, 8 and 9 is any amino
      acid
<220> FEATURE:
<221> NAME/KEY: misc_feature
<222> LOCATION: (10)..(10)
<223> OTHER INFORMATION: Xaa at position 10 is F, Y or H
<220> FEATURE:
<221> NAME/KEY: misc_feature
<222> LOCATION: (11)..(12)
<223> OTHER INFORMATION: Xaa at positions 11 and 12 is any amino acid
<220> FEATURE:
<221> NAME/KEY: misc_feature
<222> LOCATION: (14)..(14)
<223> OTHER INFORMATION: Xaa at position 14 is L, I, V, M, G or A
<220> FEATURE:
<221> NAME/KEY: misc_feature
<222> LOCATION: (16)..(17)
<223> OTHER INFORMATION: Xaa at positions 16 and 17 is L, I, V, M, F
      or A

<400> SEQUENCE: 22

Ser Glu Xaa Xaa Xaa Xaa Xaa Xaa Xaa Xaa Xaa Xaa Glu Xaa His Xaa
1               5                   10                  15

Xaa
```